(12) United States Patent
Archbold

(10) Patent No.: US 11,794,030 B2
(45) Date of Patent: *Oct. 24, 2023

(54) MAGNETIC CORE BONE SCREW

(71) Applicant: Christopher A Archbold, Mission Viejo, CA (US)

(72) Inventor: Christopher A Archbold, Mission Viejo, CA (US)

(*) Notice: Subject to any disclaimer, the term of this patent is extended or adjusted under 35 U.S.C. 154(b) by 609 days.

This patent is subject to a terminal disclaimer.

(21) Appl. No.: 16/948,907

(22) Filed: Oct. 5, 2020

(65) Prior Publication Data

US 2021/0023383 A1     Jan. 28, 2021

Related U.S. Application Data

(63) Continuation-in-part of application No. 16/919,029, filed on Jul. 1, 2020, now Pat. No. 11,510,801, which is a continuation-in-part of application No. 15/862,017, filed on Jan. 4, 2018, now Pat. No. 10,702,320.

(Continued)

(51) Int. Cl.
*A61N 2/12* (2006.01)
*A61N 2/00* (2006.01)
(Continued)

(52) U.S. Cl.
CPC ............ *A61N 2/12* (2013.01); *A61B 17/8605* (2013.01); *A61B 17/8685* (2013.01);
(Continued)

(58) Field of Classification Search
CPC . A61F 5/02; A61F 5/026; A61B 17/70; A61B 17/7062; A61B 17/86;
(Continued)

(56) References Cited

U.S. PATENT DOCUMENTS 5,425,763 A    6/1995  Stemmann
5,507,835 A    4/1996  Jore
(Continued)

OTHER PUBLICATIONS

Kheirkhah, P., Denyer, S., Bhimani, A.D. et al., Magnetic Drug Targeting: A Novel Treatment for Intramedullary Spinal Cord Tumors, Scientific Reports, Jul. 30, 2018, pp. 1-9.
(Continued)

*Primary Examiner* — Christopher J Beccia
(74) *Attorney, Agent, or Firm* — CIONCA IP Law P.C.; Marin Cionca

(57) ABSTRACT

A screw cap removably associated with a bone screw, the bone screw comprising: a head having a set of interior threads, one of the set of interior threads having a circular slot; a magnet; and an interior cavity located within the bone screw and configured to house the magnet; the screw cap comprising: a top end configured to receive a driving means for inserting the screw cap into, and removing the screw cap from, the head; a body having a set of cap threads, one of the set of cap threads comprising a locking bead; and an annular recess concentrically lining a portion of the body, the annular recess comprising a leakage ring for establishing a seal between the screw cap and the head; wherein an association of the set of cap threads with the set of interior threads causes the locking bead to be engaged with the circular slot.

23 Claims, 20 Drawing Sheets

Related U.S. Application Data

(60) Provisional application No. 62/535,706, filed on Jul. 21, 2017, provisional application No. 62/986,120, filed on Mar. 6, 2020.

(51) Int. Cl.
   *A61B 17/86* (2006.01)
   *A61L 31/02* (2006.01)
   *A61L 31/04* (2006.01)
   *A61L 31/06* (2006.01)
   *A61B 17/00* (2006.01)

(52) U.S. Cl.
   CPC ........... *A61L 31/022* (2013.01); *A61L 31/049* (2013.01); *A61L 31/06* (2013.01); *A61N 2/004* (2013.01); *A61B 2017/00876* (2013.01)

(58) Field of Classification Search
   CPC . A61B 17/8605; A61B 17/861; A61B 17/864; A61B 17/8625; A61B 17/8635
   See application file for complete search history.

(56) References Cited

U.S. PATENT DOCUMENTS

| | | | |
|---|---|---|---|
| 5,741,336 | A | 4/1998 | Fraser |
| 6,387,096 | B1 | 5/2002 | Tyde, Jr. |
| 8,029,570 | B2 | 10/2011 | Barnes et al. |
| 8,568,457 | B2 | 10/2013 | Hunziker |
| 8,579,947 | B2 | 11/2013 | Wu |
| 10,702,320 | B2 * | 7/2020 | Archbold ............ A61B 17/8625 |
| 11,510,801 | B2 * | 11/2022 | Archbold ................ A61F 5/026 |
| 2003/0236572 | A1 | 12/2003 | Bertram, III |
| 2004/0059423 | A1 * | 3/2004 | Barnes ..................... A61N 2/06 |
| | | | 600/12 |
| 2006/0074448 | A1 | 4/2006 | Harrison et al. |
| 2006/0079897 | A1 | 4/2006 | Harrison et al. |
| 2008/0255556 | A1 | 10/2008 | Berger |
| 2009/0099404 | A1 * | 4/2009 | Kraus .................... A61B 17/86 |
| | | | 623/18.11 |
| 2014/0025122 | A1 | 1/2014 | Cook et al. |
| 2016/0242820 | A1 * | 8/2016 | Whipple ............ A61B 17/8685 |
| 2019/0070426 | A1 | 3/2019 | Alam |

OTHER PUBLICATIONS

Yun-Gang Luo, Tao Yu, Guo-Min Liu, and Nan Yang. Study of Bone-screw Surface Fixation in Lumbar Dynamic Stabilization. Chinese Medical Journal, Feb. 5, 2015; 368-372, 128 (3), Wolters Kluwer Health, China, https://www.ncbi.nlm.nih.gov/pmc/articles/PMC4837868/.

Self-Sealing Fastener Products, ZaGO Manufacturing Company, Inc. http://www.sealingscrews.com/Self-SealingProducts.asp.

* cited by examiner

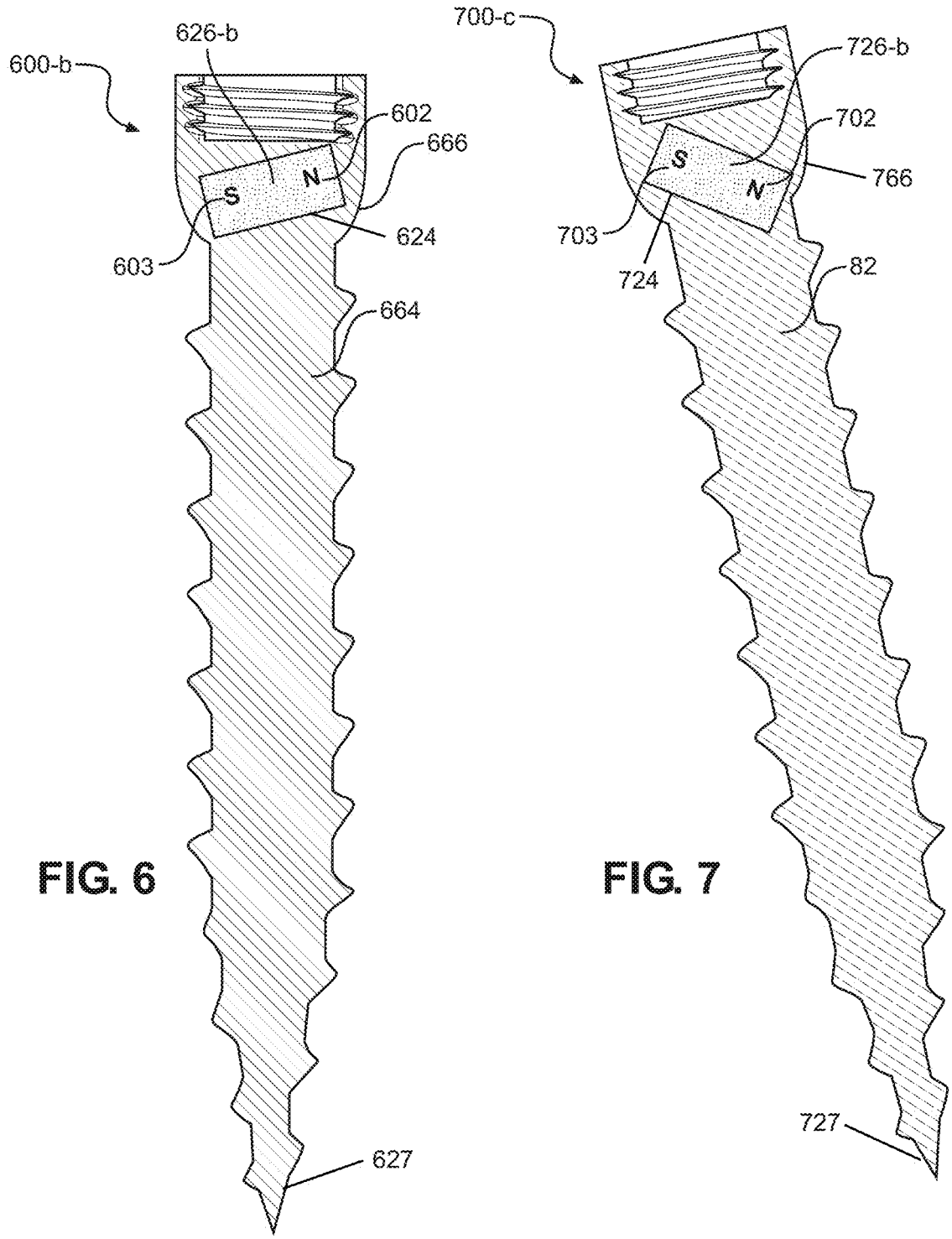

MAGNETIC CORE BONE SCREW

CROSS-REFERENCE TO RELATED APPLICATIONS

This application is a continuation-in-part of and claims the benefit of U.S. Non-Provisional application Ser. No. 16/919,029, filed Jul. 1, 2020, which claimed the benefit of U.S. Non-Provisional application Ser. No. 15/862,017, filed Jan. 4, 2018, which claimed the benefit of U.S. Provisional Application No. 62/535,706, filed Jul. 21, 2017, and claimed the benefit of U.S. Provisional Application No. 62/986,120, filed Mar. 6, 2020, which are hereby incorporated by reference, to the extent that they are not conflicting with the present application.

BACKGROUND OF INVENTION

1. Field of the Invention

The invention relates generally to surgical and orthopedic devices and more specifically to bone screws and methods and systems involving said bone screws.

2. Description of the Related Art

Magnets implanted in bones during surgery on the bones may be used for correcting problems in patients' bones. These problems may include bones pressing on nerves in the spinal column, for example, but procedures to implant magnets may often require additional materials such as brackets or other similar apparatuses to hold the magnets in place, or may require several steps to implant the magnets inside the bones. These types of procedures may be invasive and may also introduce the risk of rejection of the implanted materials by the body. Ferrous magnetic screws including strong neodymium magnetic screws used for such procedures may be subject to rejection when implanted in the body. Coatings placed on the magnets to prevent such rejection may also wear off over time. Such procedures can thus cause potential problems to the patient, or may not be suitable options for certain patients.

Scoliosis, as is known to those of ordinary skill in the art, is a disorder that causes an abnormal curve to develop in the spine or backbone. Typically diagnosed by visual inspection of the patient's spine, scoliosis can cause the head to appear off center, and the curve in the spine can cause twisting of the vertebrae and ribs. Scoliosis can affect patients on varying levels of severity. In severe cases of scoliosis, where the curve of the spine is at an angle greater than 50 degrees, the heart and the lungs may function irregularly, causing shortness of breath and chest pain. Additionally, severe types of scoliosis can cause back pain, rib pain, neck pain, muscle soreness and even abdominal pain.

Less severe cases of scoliosis can be treated with observation and bracing. More severe types of scoliosis (e.g., neuromuscular scoliosis), however, normally cannot be treated with observation and bracing alone. Currently, these more severe types of scoliosis in the spine are treated surgically. The surgery, which aims to correct the curve of the back to as close to normal as possible, involves performing a spinal fusion. Spinal fusion surgery involves implanting a combination of screws, hooks and/or rods into the curved bones of the spine to hold the curved bones in place and to prevent any further curving of the spine. Autograft bone material is then placed between the curved vertebrae to fuse the vertebrae together as the curvature is corrected.

While spinal fusion is a popular and usually successful procedure, the procedure is invasive and leads to scarring of the patient's back. Furthermore, this surgical method may lead to complications such as infection, and the rods implanted in the back could break over time, requiring further surgery. Additionally, the fused portion of the spine will be permanently stiff due to the resultant fusion of the vertebrae. Such permanent back stiffness may inhibit flexibility and may make certain activities difficult to perform.

Therefore, there is a need to solve the problems described above by providing a magnetic core bone screw, and a surgical method of use, for correcting bone-related issues.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a bone screw configured to be screwed into a bone is provided, comprising: an exterior casing; a head having a head interior surface; a tip having a point configured to be driven into the bone; a shaft extending between the head and the tip; a magnet having a north pole and a south pole; an interior cavity within the bone screw configured to house the magnet; a cap having: a top end having a recess configured to receive a means for driving the bone screw into the bone; and a bottom end having a set of cap threads; wherein the exterior casing encloses the tip, the shaft, at least a portion of the cap, and at least a portion of the head, and wherein a portion of the exterior casing enclosing the shaft comprises a set of exterior threads; the head being configured to receive the cap by having a set of interior threads on the head interior surface; and wherein an association of the set of cap threads with the set of interior threads causes the cap to be sealed to the head, and thus causes the magnet to be encased within the bone screw with no portion of the magnet exposed outside of the exterior casing. An advantage may be that a plurality of magnetic core bone screws may be used for aligning bones of the body into a correct physiologic position using a minimally invasive surgical technique, without the need for brackets or additional apparatuses to connect the screws to the bones, and without the need for additional steps in the surgery to apply such brackets. Another advantage may be that the complete encasing of the magnet within the screw may reduce the potential for rejection by the body, such that implantation of strongly magnetic material into the bone using a minimally invasive technique may be achieved while reducing risk of rejection of the implanted materials in the patient. Another advantage may be that orthopedic movement of the bones may be achieved with a minimally invasive surgical technique with fewer steps than is required by techniques known in the art.

In another aspect, a bone screw configured to be screwed into a bone is provided, comprising: an exterior casing; a head having a recess on a top end, the recess being configured to receive a means for driving the bone screw into the bone; a tip having a point configured to be driven into the bone; a shaft extending between the head and the tip; a magnet having a north pole and a south pole; an interior cavity within the bone screw configured to house the magnet, the interior cavity being located inside of the shaft, such that a length of the magnet extending between the north pole and the south pole is parallel to the shaft; wherein the exterior casing encloses the tip, the shaft, and the head, and wherein a portion of the exterior casing enclosing the shaft comprises a set of exterior threads; and wherein the magnet is encased within the bone screw with no portion of the magnet exposed outside of the exterior casing. Again, an advantage may be that a plurality of magnetic core bone screws may be used for aligning bones of the body into a correct physiologic position using a minimally invasive surgical technique, without the need for brackets or additional apparatuses to connect the screws to the bones, and without the need for additional steps in the surgery to apply such brackets. Another advantage may be that the complete encasing of the magnet within the screw may reduce the potential for rejection by the body, such that implantation of strongly magnetic material into the bone using a minimally invasive technique may be achieved while reducing risk of rejection of the implanted materials in the patient. Another advantage may be that orthopedic movement of the bones may be achieved with a minimally invasive surgical technique with fewer steps than is required by techniques known in the art.

In an aspect, a magnetic ball core bone screw is provided for implanting into bone for the correction of scoliosis of the spine. The magnetic ball core bone screw may comprise: an exterior casing; a head configured to receive a means for driving the bone screw into the bone; a tip having a distalmost point configured to be driven into the bone; a shaft extending between the head and the tip; a free-rolling magnetic ball having a north pole and a south pole; an interior cavity located within the shaft and configured to house the magnetic ball; wherein the exterior casing encloses the tip, the shaft, and at least a portion of the head, and wherein a portion of the exterior casing enclosing the shaft comprises a set of exterior threads; and wherein the magnetic ball is fully encased within the bone screw, such that no portion of the magnetic ball is exposed outside of the exterior casing. An advantage may be that a plurality of magnetic core bone screws may be used for aligning vertebrae of the spine into a correct physiologic position using a minimally invasive surgical technique, without the need for brackets or additional apparatuses to connect the screws to the bones, and without the need for additional steps in the surgery to apply such brackets. Another advantage may be that the complete encasing of the magnetic ball within the screw may reduce the potential for rejection by the body, such that implantation of strongly magnetic material into the bone using a minimally invasive technique may be achieved while reducing risk of rejection of the implanted materials in the patient.

In an aspect, a magnetic ball core bone screw is provided for implanting into bone for the correction of scoliosis of the spine. The magnetic ball core bone screw may comprise: a head having a set of interior threads; a tip having a distalmost point configured to be driven into the bone; a body extending between the head and the tip, the body comprising a set of exterior threads; a free-rolling magnetic ball having a north pole and a south pole; an interior cavity located within the head and configured to house the magnetic ball; a cap having: a top end configured to receive a means for driving the bone screw into the bone; and a bottom end having a set of cap threads; wherein an association of the set of cap threads with the set of interior threads causes the cap to be sealed to the head, and thus causes the magnetic ball to be fully encased within the bone screw, such that no portion of the magnetic ball is exposed outside of the bone screw. An advantage may be that a plurality of magnetic core bone screws may be used for aligning vertebrae of the spine into a correct physiologic position using a minimally invasive surgical technique, without the need for brackets or additional apparatuses to connect the screws to the bones, and without the need for additional steps in the surgery to apply such brackets. Another advantage may be that the complete encasing of the magnetic ball within the screw may reduce the potential for rejection by the body, such that implantation of strongly magnetic material into the bone using a minimally invasive technique may be achieved while reducing risk of rejection of the implanted materials in the patient.

In another aspect, a system for correcting scoliosis of the spine is provided with at least one magnetic ball core bone screw and an external correction abacus. The at least one magnetic ball core bone screw may comprise a free-rolling magnetic ball provided inside an internal cavity of the bone screw, and the bone screw may be configured to be driven into bone. The external correction abacus may be configured to be worn on a user's back and may comprise: a frame having interior walls, a plurality of rods extending horizontally between the interior walls, and at least one pair of magnetic riders configured to be mounted onto at least one of plurality of rods. The at least one pair of magnetic riders may comprise a first fixed rider and a second free rider. The first fixed rider may be provided with an attracting magnet and a locking screw adapted to secure the fixed rider to the at least one of the plurality of rods. The second free rider may be provided with a front-facing magnet and a side-facing magnet, wherein the side-facing magnet faces toward and is pulled by the attracting magnet. The front facing magnet may simultaneously face toward the at least one bone screw implanted in a vertebra of the spine, such that the front-facing magnet may magnetically pull on the at least one magnetic ball core bone screw. Thus, an advantage of the scoliosis correction system is that the magnetic ball core bone screws may be used with or without the correction abacus to realign the spinal column. An additional advantage is that the correction abacus does not need to be surgically implanted into the patient's spine, thus reducing the risk of any potential infection or complications. An additional advantage is that the correction abacus may be made from readily available materials and is therefore cost-effective.

In another aspect, a system for correcting scoliosis of the spine is provided with at least one magnetic ball core bone screw and a magnetic girdle. The at least one magnetic ball core bone screw may comprise a free-rolling magnetic ball provided inside an internal cavity of the bone screw, and the bone screw may be configured to be driven into bone. The magnetic girdle may be configured to be worn on a user's torso and may comprise: a stretchable body having shoulder straps and sets of top and bottom belt loops, a flexible hose extending vertically along an interior rear of the stretchable body, and a plurality of magnets disposed within the flexible tube, each magnet of the plurality of magnets being arranged in an identical orientation. The plurality of magnets may each comprise a north pole and a south pole, such that a continuous magnetic field is formed along the flexible hose. The magnetic girdle may further comprise a plurality of dividers disposed within the flexible hose, each divider of the plurality of dividers being positioned between adjacent magnets, such that an equal separation is maintained between the adjacent magnets. The plurality of magnets, when the magnetic girdle is worn, may magnetically pull on the magnetic ball of the at least one bone screw implanted in the spine. Thus, an advantage is that the magnetic hose girdle may help correct the curvature of a spine having scoliosis without the need for additional surgery. An additional advantage is that the flexible hose may comfortably be kept in close proximity to the spine having scoliosis, such that to enable the curved vertebrae having magnetic ball core bone screws to be shifted into proper alignment. Another advantage is that the magnetic hose girdle may allow a user to naturally bend over or stretch to the side while maintaining magnetic attraction between the plurality of magnets and the bone screws implanted in the spine. Another advantage is that the magnetic hose girdle may be conveniently and easily worn by the user and later removed, as needed.

In another aspect, a bone screw configured to be screwed into a bone is provided, comprising: an exterior casing; a head having a set of interior threads, the head being configured to receive a first driving means for driving the bone screw into the bone; wherein one of the set of interior threads comprises a circular slot; a tip having a distalmost point configured to be driven into the bone; a shaft extending between the head and the tip; a magnet having a north pole and a south pole; an interior cavity disposed within the bone screw and configured to house the magnet; and a cap removably associated with the head, the cap comprising: a top end configured to receive a second driving means for inserting the cap into, and removing the cap from, the head; a body having a set of cap threads, one of the set of cap threads comprising a locking bead; and a leakage ring concentrically lining an upper portion of the body; wherein the exterior casing encompasses the tip, the shaft, and at least a portion of the head, and wherein a portion of the exterior casing encompassing the shaft comprises a set of exterior threads; and wherein an association of the set of cap threads with the set of interior threads causes the locking bead to be engaged with the circular slot, and thus causes the leakage ring to be compressed within an interior of the head, resulting in the cap being sealed to the head. Thus, an advantage is that the locking bead and the corresponding circular slot may thus provide the disclosed bone screw with a failsafe, such that to ensure the screw cap remains locked within the screw head during use. Another advantage may be that the complete encasing of the magnetic ball within the screw may reduce the potential for rejection by the body, such that implantation of strongly magnetic material into the bone using a minimally invasive technique may be achieved while reducing risk of rejection of the implanted materials in the patient. An additional advantage is that the screw cap may safely and securely be removed from the screw head without altering the position of the bone screw already implanted into bone.

In another aspect, a bone screw configured to be screwed into a bone is provided, comprising: a head having a set of interior threads, at least one of the set of interior threads having a circular slot; a tip having a distalmost point configured to be driven into the bone; a body comprising a set of exterior threads, the body extending between the head and the tip; a magnet having a north pole and a south pole; an interior cavity located within the bone screw and configured to house the magnet; and a cap removably associated with the head, the cap comprising: a top end configured to receive a driving means for inserting the cap into, and removing the cap from, the head; and a set of cap threads lining a bottom of the cap, at least one of the set of cap threads comprising a locking bead; wherein an association of the set of cap threads with the set of interior threads causes the locking bead to be engaged with the circular slot, and thus causes the cap to be sealed to the head, such that the magnet is fully encased within the bone screw. Thus, an advantage is that the locking bead and the corresponding circular slot may thus provide the disclosed bone screw with a failsafe, such that to ensure the screw cap remains locked within the screw head during use. Another advantage may be that the complete encasing of the magnetic ball within the screw may reduce the potential for rejection by the body, such that implantation of strongly magnetic material into the bone using a minimally invasive technique may be achieved while reducing risk of rejection of the implanted materials in the patient. An additional advantage is that the screw cap may safely and securely be removed from the screw head without altering the position of the bone screw already implanted into bone.

In another aspect, a screw cap removably associated with a bone screw is provided, the bone screw comprising: a head having a set of interior threads, at least one of the set of interior threads having a circular slot; a magnet; and an interior cavity located within the bone screw and configured to house the magnet. The screw cap may comprise: a top end configured to receive a driving means for inserting the screw cap into, and removing the screw cap from, the head; a body having a set of cap threads, at least one of the set of cap threads comprising a locking bead; and an annular recess concentrically lining an upper portion of the body, the annular recess comprising an integral leakage ring for establishing a liquid-proof seal between the screw cap and the head; wherein an association of the set of cap threads with the set of interior threads causes the locking bead to be engaged with the circular slot, and thus causes the leakage ring to be compressed within an interior of the head, resulting in the screw cap being sealed to the head. Thus, an advantage is that the locking bead and the corresponding circular slot may thus provide the disclosed bone screw with a failsafe, such that to ensure the screw cap remains locked within the screw head during use. Another advantage may be that the complete encasing of the magnetic ball within the screw may reduce the potential for rejection by the body, such that implantation of strongly magnetic material into the bone using a minimally invasive technique may be achieved while reducing risk of rejection of the implanted materials in the patient. An additional advantage is that the screw cap may safely and securely be removed from the screw head without altering the position of the bone screw already implanted into bone.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which:

FIG. 6 illustrates a side sectional view another example of the magnetic core bone screw, having a magnet placed at an angle inside the screw head, according to an aspect.

FIG. 7 illustrates a side sectional view of another example of the magnetic core bone screw having a magnet placed at an angle inside the screw head, according to an aspect.

DETAILED DESCRIPTION

Figures 1A, 1B:
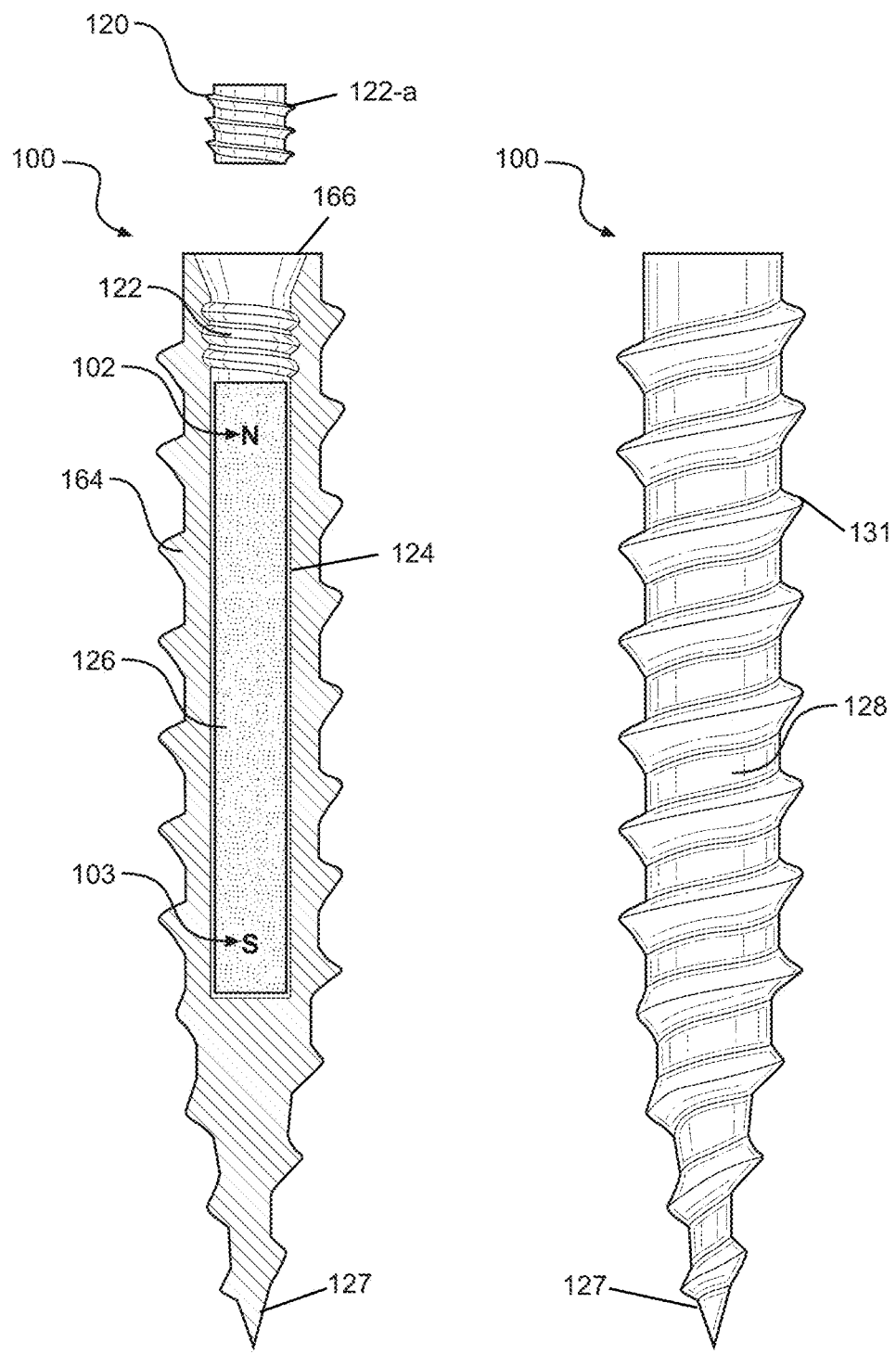
FIGS. 1A-1B illustrate a side sectional view and a side view, respectively, of a magnetic core bone screw, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

For the following description, it can be assumed that most correspondingly labeled elements across the figures (e.g., 103 and 403, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

FIGS. 1A-1B illustrate a side sectional view and a side view, respectively, of a magnetic core bone screw ("magnetic core bone screw," or "bone screw") 100, according to an aspect. Bone screws 100 containing magnetic cores may screwed into the vertebrae or other bones of the body with a screwdriver, for example, or any other suitable means. The bone screw 100 may include a head 166, which may be associated with a screw cap 120, a shaft 164, and a distal-most tip 127 at the opposite end of the head 166 which may be pointed to aid in the drilling and the insertion of the bone screw 100 into a bone. The shaft 164 may extend between the head 166 and the tip 127. The bone screw may be provided with an inner cavity or chamber 124 for housing a magnet 126, which may thus become the magnetic core 126 ("magnetic core," or "magnet") of the bone screw. The magnet 126 may, for example, be neodymium, or any other suitable material. As an example, the magnetic core 126 may be housed within a chamber 124 located in the shaft 164 of the bone screw 100. The magnet 126 having a north pole 102 and a south pole 103 may be placed in the interior cavity 124 of the bone screw 100 as shown in FIG. 1A such that the magnet is not visible from the exterior of the screw, as shown by FIG. 1B. The exterior casing 128 of the screw 100, which may completely surround and encase the magnet 126, may be constructed from a material not likely or less likely to be rejected by the human body, such as, for example, titanium or ceramic materials. An advantage may be that additional coatings may not be needed on the magnet itself, thus again reducing the risk of rejection of materials by the patient's body. A complete encasing of the magnet 126 by the exterior casing 128 may thus reduce the risk to a patient of injury, rejection of implanted materials, or complications following a surgery.

The bone screw 100 may also be provided with interior threads 122 at a top end of the screw at the head 166, and the inner threads 122 may be threaded or associated with the cap threads of 122-*a* of a top screw cap ("top screw cap," "screw cap" or "cap") 120. The cap 120 may then seal in the magnet 126 such that no portion of the magnet is exposed or visible outside of the exterior casing 128 of bone screw 100, and the cap may be constructed from the same or similar material as the exterior casing 128. The cap 120 may allow for the magnet 126 to be removably inserted into the bone screw, and replaced or repositioned as needed, for example. As shown by FIG. 1B, the bone screw 100 may be provided with exterior threads 131 on the exterior casing 128 surface, which may aid a user in screwing, drilling, or inserting the bone screw 100 into bone.

The magnetic core bone screws 100 may be used to help relocate or align bones to the correct anatomical position, to correct problems or to relieve pain or pressure, for example. As examples, the screws may be used to align vertebrae, or to separate vertebrae that are pinching a nerve. For example, for patients or users suffering from an undesired curvature of the spine, the magnetic core bone screws 100 may be placed in several vertebrae in series such that the vertebral column may be brought into a proper or desired alignment. Magnetic core bone screws 100 may be used as a part of a minimally invasive surgical technique. An advantage may be that this method of implanting magnets into bones may require fewer steps to complete the operation than other known methods. As an example, the magnetic core bone screws 100 may be placed into vertebrae, or any other suitable bones of the body. In the spine, orthopedic movement of vertebrae may be achieved by using magnetic core screws inserted into the vertebrae to attract or repel adjacent magnetic core screws screwed into neighboring vertebrae. The magnetic core bone screws may also be used alone or in tandem with other therapies to align the spine for those that suffer from improper curvature such as that which may occur in scoliosis. For example, another therapy or technique that the magnetic core bone screws may be used with is the attachment or placement of external magnets, which may be strapped into fixed positions outside of the body of the patient or the user, which may assist in bringing bones which have magnetic core bone screws drilled into them into a proper or desired position or alignment over time. As another example of an additional therapy or technique that may be used with magnetic core bone screws drilled into a patient's bones, the body or a portion of the body may be placed into an external electromagnetic field which may be used to bring bones containing the magnetic core bone screws into a proper or desired position or alignment. As another example, a patient or user suffering from bones that are too short may have magnetic core bone screws drilled into their bones, and next be placed into an external electromagnetic field in order to lengthen the bone by taking advantage of the magnetic pull on each end of the drilled bones, over time.

Another advantage may be that this minimally invasive technique may require no brackets or other apparatuses to be attached to the bones or vertebrae, thus requiring less materials and less potential risk of rejection of the inserted materials in the patient. Brackets for holding a magnet to the bones may be eliminated from the process, and multiple steps for inserting a magnet into the bone may be reduced only to the step of screwing the bone screw with an embedded or encased magnet into the bone. Thus, another advantage may be that these surgical procedures may be more efficient than previously known techniques.

The magnetic core bone screws may be constructed to be the size of conventional bone screws as known in the art, or may be constructed to be slender enough to fit through the thickness of a hypodermic needle. Another advantage may be that the magnet embedded within the bone screw may require no additional coating, being encased completely within the bone screw itself.

Figure 2:
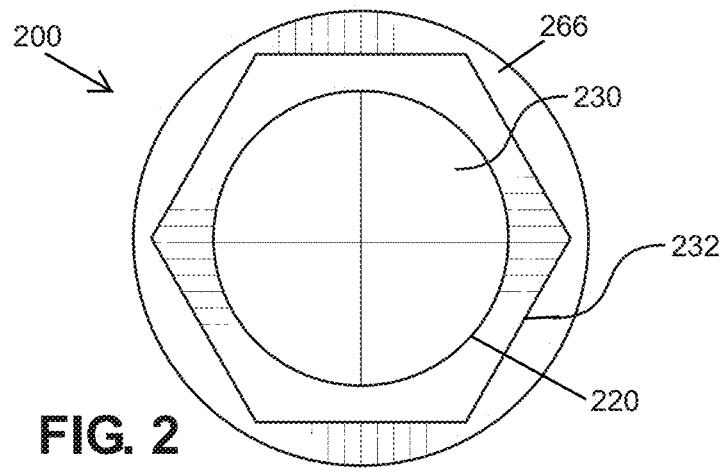
FIG. 2 illustrates the top view of the screw cap on a bone screw, according to an aspect.

FIG. 2 illustrates the top view of the screw cap ("screw cap" or "cap") 220 on a bone screw 200, according to an aspect. As an example, the screw cap 220 may be provided with a recess or screw drive, configured to receive any means or tool for driving the bone screw 200 into a bone. As an example, the bone screw may be provided with a recess or screw drive such as, for example, a Phillips head as shown by 230, or any other suitable type of screw drive. The bone screw 200 may also be constructed such that the screw head 266 comprises a screw drive, such as an Allen's head 232 shown as an example, or any other suitable type of screw drive, which may be used for receiving a means for driving the screw 200 into the bone. It should be understood that the screw cap and the screw head may each independently comprise a recess or screw drive for the removal of the bone screw from the bone without the removal of the screw cap, as an example. Furthermore, the separate screw drives 230, 232 may enable the removal of the screw cap 220 (for replacing of the internal magnet, for example) from the screw head 266 without removal of the bone screw 200 from the bone, as an example.

Figure 3:
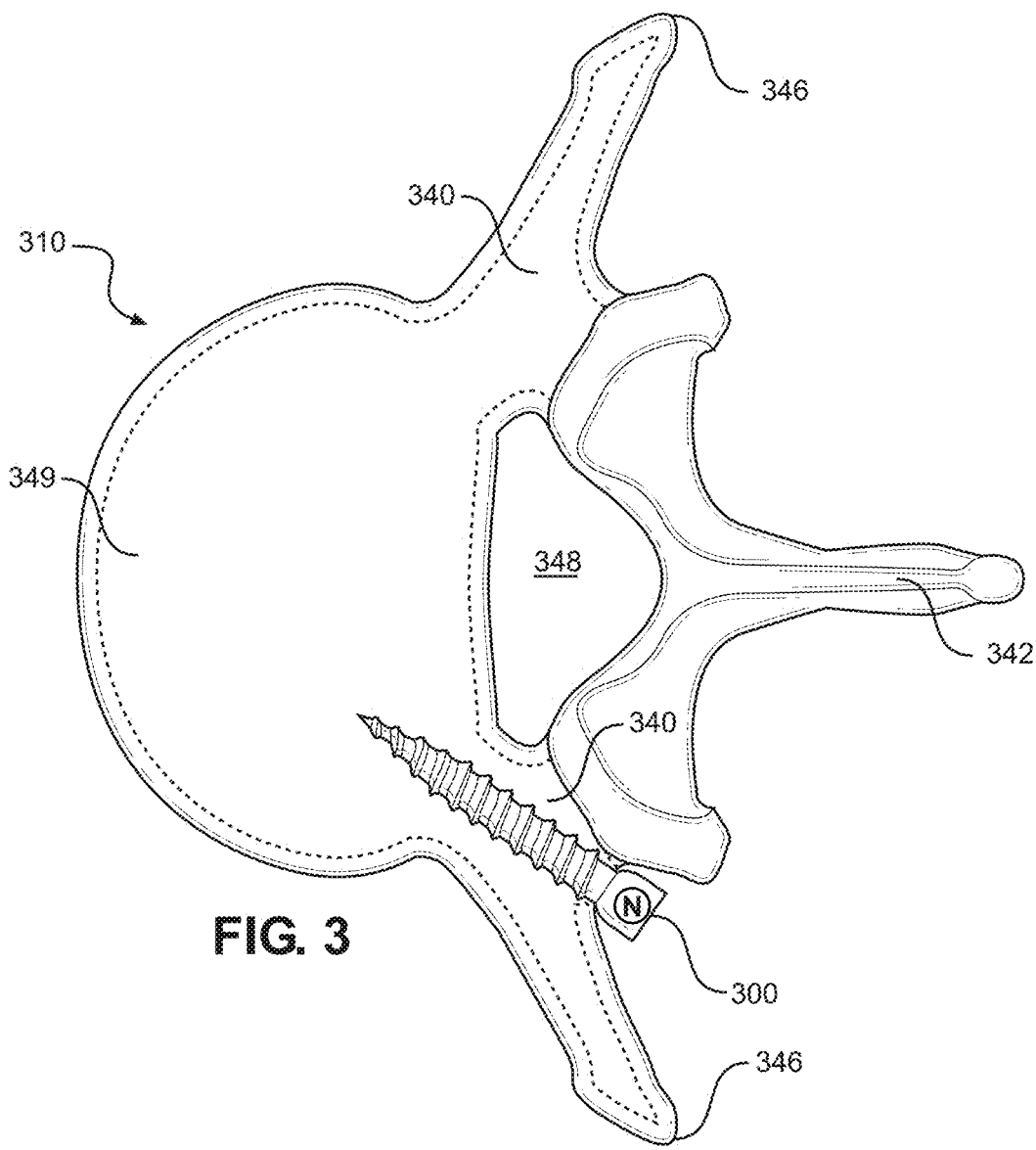
FIG. 3 illustrates the superior (top) view of a vertebra with a magnetic core bone screw 300 screwed into the interior of the vertebral body of the vertebral bone, according to an aspect.

FIG. 3 illustrates the superior (top) view of a vertebra 310 with a magnetic core bone screw 300 screwed into the interior of the vertebral body 349 of the vertebral bone 310, according to an aspect. The spinous process 342, transverse processes 340, the tip of the transverse processes 346, the vertebral foramen 348, and the vertebral body 349 may be visible from the superior view of the vertebra, as shown. The magnet (not visible) within the magnetic core bone screw 300 may be located in the shaft of the magnetic core bone screw (as shown by 126 in FIG. 1A).

The bone screw 300 having a magnet may be screwed into the vertebrae 310 in order to take advantage of or employ the attraction and repulsion characteristics of magnetic fields. These forces may be used to align vertebrae, separate vertebrae or bring vertebrae closer together, according to the medical needs of the user. These forces may be used to bring bones of the body closer together or farther apart. These techniques may be used alone or in combination with other conventional orthopedic techniques for either minor or major bone or vertebral movement, for example. The magnetic core bone screw 300 may be placed anywhere into a bone, such as a vertebra, for example, such that the magnetic forces of the screws may produce the desired result. As an example, for achieving a correct positioning of the vertebrae, a magnetic core bone screw or a plurality of screws may normally be screwed into a vertebra, and an additional screw or plurality of screws may be screwed into an accompanying nearby vertebra, to creates the repulsion or attraction force that move the vertebrae to the desired position. The magnetic core bone screws 300 may be screwed into several vertebrae in series to achieve the desired result for the vertebral column. Magnetic core bone screws may also be screwed into other bones of the body to similarly attain and/or retain the proper physiologic placement of the bones.

Figure 4:
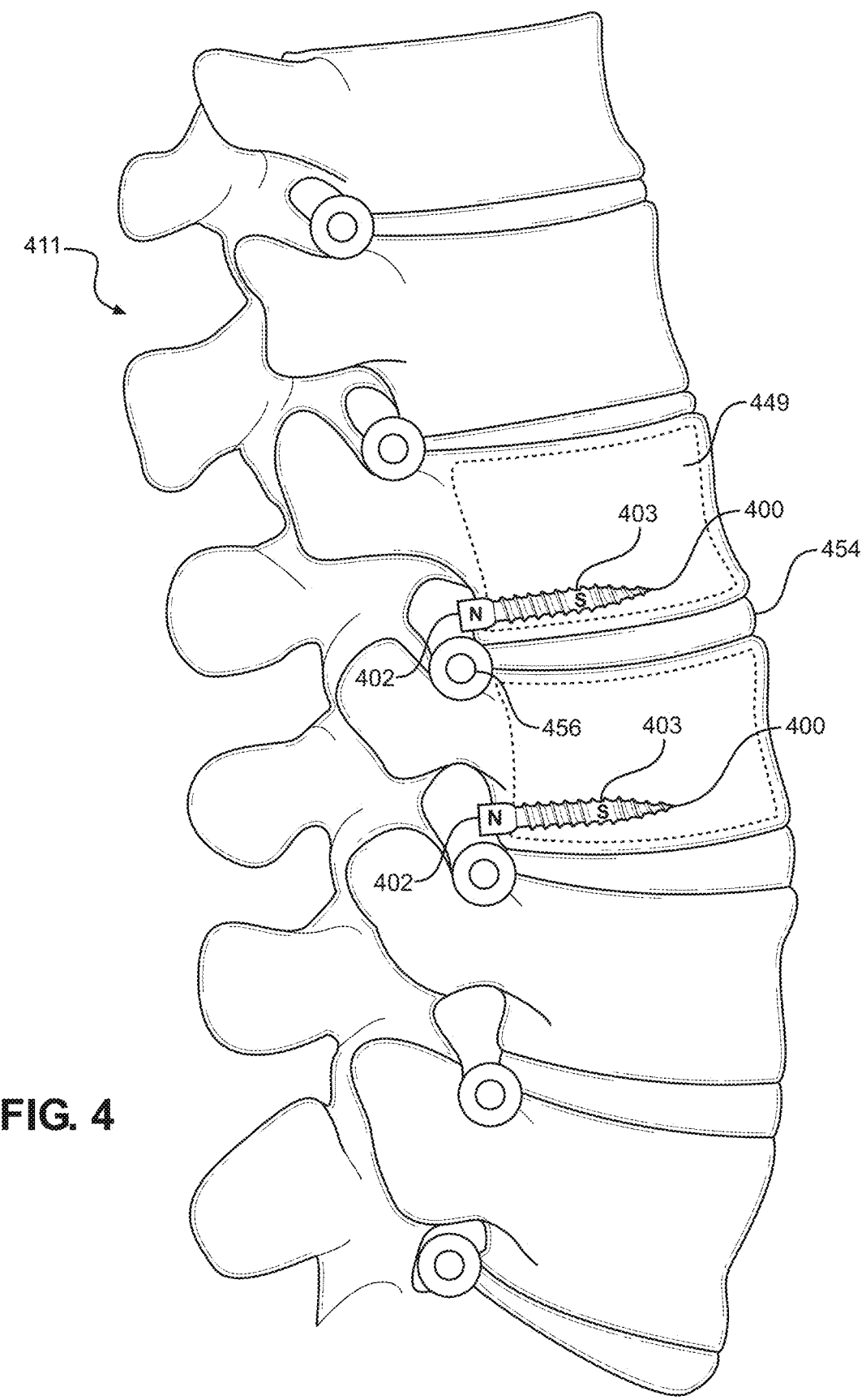
FIG. 4 illustrates the lateral (side) view of the spinal column with inserted magnetic core bone screws, according to an aspect.

FIG. 4 illustrates the lateral (side) view of the spinal column 411 with inserted magnetic core bone screws 400, according to an aspect. The body 449 of the individual vertebra, the intervertebral disc 454, and the spinal nerve 456 are visible in this exemplary view. The repulsion of the magnets inside the magnetic core bone screws 400 may help to relieve pressure on the spinal nerve 456. Again, the magnetic core bone screws 400 may have the magnets located inside the shaft of the screws. An exemplary alignment of the north and south poles of the magnets are shown by 402 and 403, respectively. A plurality of bone screws 400 may be inserted into the vertebrae with their north poles 402 and south poles 403 aligned such that a repulsion is caused between the magnets.

Figures 5A, 5B:
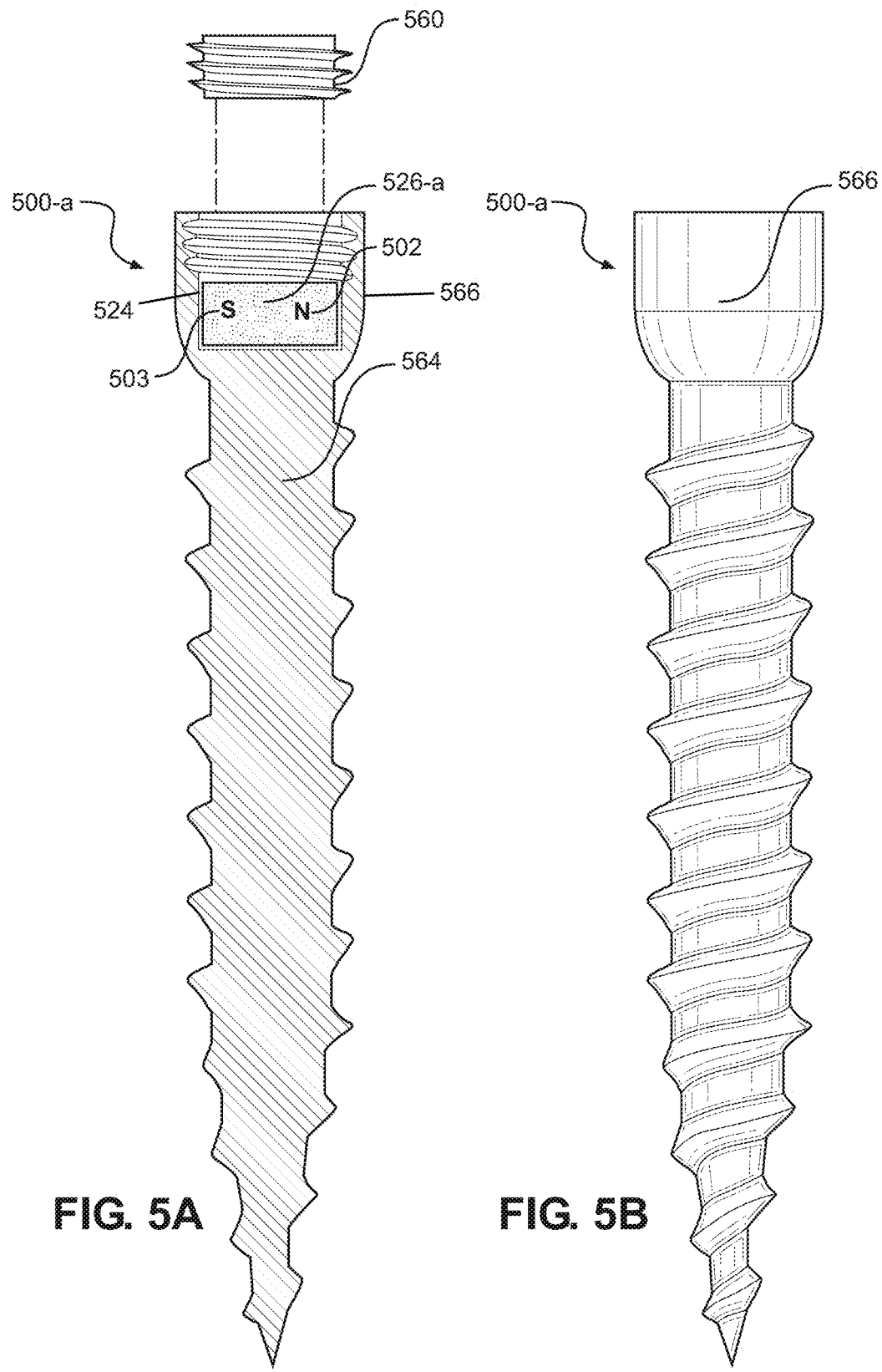
FIGS. 5A-5B illustrate a side sectional view and a side view, respectively, of another example of a magnetic core bone screw having a magnetic core located inside the head of the screw, according to an aspect.

FIGS. 5A-5B illustrate a side sectional view and a side view, respectively, of another example of a magnetic core bone screw 500-*a* having a magnetic core located inside the head 566 of the screw 500-*a*, according to an aspect. The magnet 526-*a* may be positioned perpendicular to the shaft 564 of the screw at a 90-degree angle, as shown, and may have a north pole 502 and south pole 503. The floor of the interior cavity 524 may be perpendicular to the shaft, such that the length of the magnet extending between the north pole and south pole housed within the cavity is perpendicular to the shaft. The bone screw 500-*a* may be provided with a screw-on cap 560, for example, which may be used for sealing in the magnet 526-*a*.

FIG. 6 illustrates a side sectional view another example of the magnetic core bone screw 600-*b*, having a magnet 626-*b* placed at an angle inside the screw head 666, according to an aspect. As an example, a magnetic core bone screw 600-*b* may have a magnet 626-*b* located within the screw head 666 rather than the shaft 664. The cavity 624 for housing the magnet may thus be within the screw head 666, and the interior cavity may have a floor that is sloped such that the cavity is at an angle other than 90 degrees to the shaft 664 of the bone screw 600-*b*. The interior cavity may be at an angle greater than 90 degrees with respect to the shaft 664, for example. Such an orientation of the magnet 626-*b* within the interior cavity 624 may allow the magnetic field of the magnet 626-*b* to be directed at various angles when screwed into the bone, as needed by the user. The angle of the magnet 626-*b* may be such that the north pole 602 is pointed upwards towards the head 666, and the south pole 603 is pointed downwards towards the tip 627, as an example.

FIG. 7 illustrates a side sectional view of another example of the magnetic core bone screw 700-*c* having a magnet 726-*b* placed at an angle inside the screw head 766, according to an aspect. As another example, and similar to the example showed in FIG. 6, the magnet 726-*b* may be placed with its north pole 702 pointing downwards towards the tip 727 and its south pole 703 pointing upwards towards the head 766, by being housed inside of a cavity 724 with a sloped floor.

Figure 8:
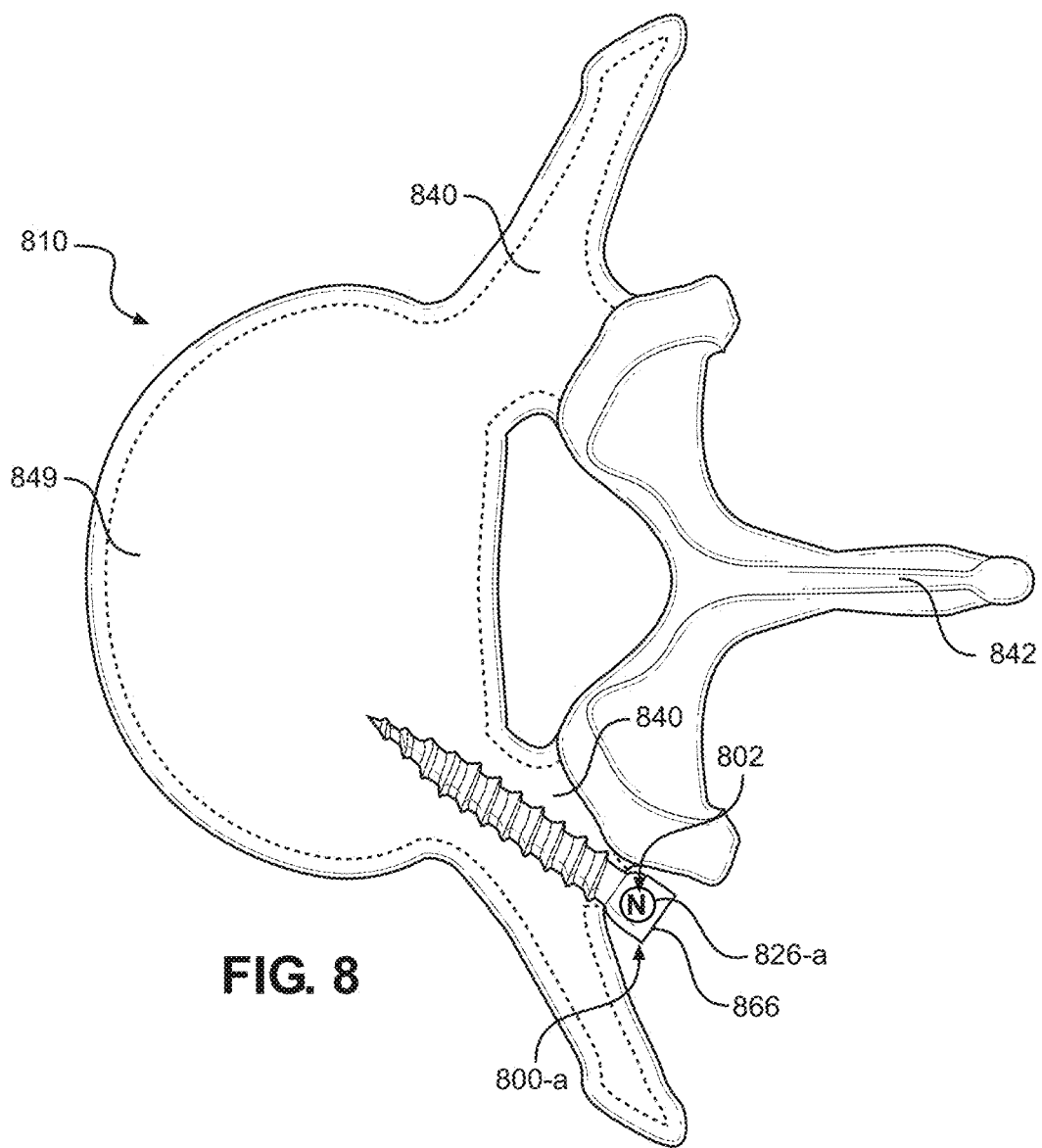
FIG. 8 illustrates the superior (top) view of a vertebra with a magnetic core bone screw 800-a screwed into the interior of the vertebral bone body, according to an aspect.

FIG. 8 illustrates the superior (top) view of a vertebra 810 with a magnetic core bone screw 800-*a* screwed into the interior of the vertebral bone body 849, according to an aspect. The transverse processes 840 and the spinous process 842 of the vertebra 810 are visible in this exemplary view. The magnetic core bone screw 800-*a* may have the magnet 826-*a* located in the interior of the head 866 of the screw 800-*a*, and the north pole 802 of the magnet may be pointed towards the superior side of the vertebra 810 with the south pole of the magnet (not visible) may be pointed towards the inferior side of the vertebra, as an example.

Figure 9:
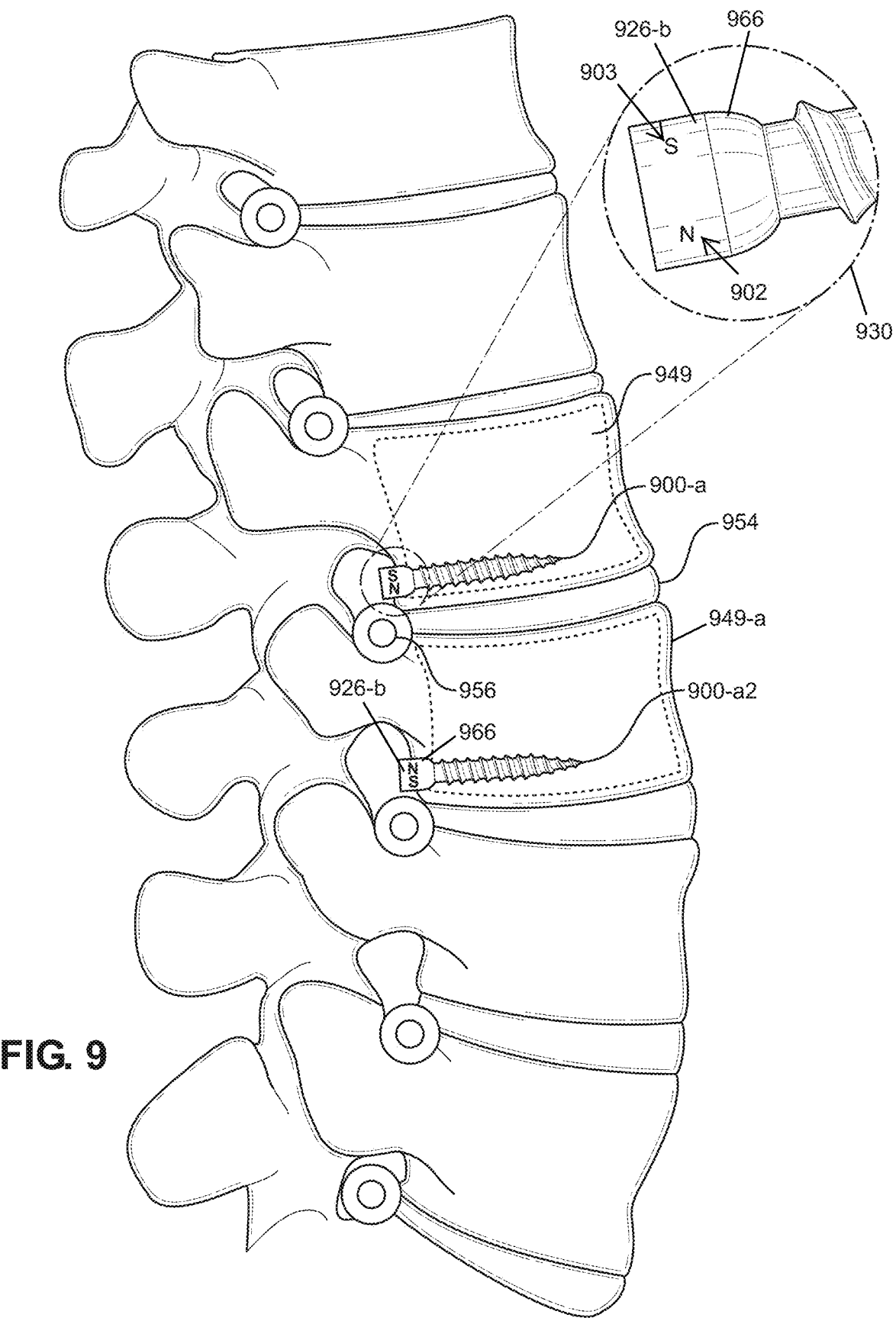
FIG. 9 illustrates another example of the lateral (side) view of the spinal column having magnetic core bone screws inserted, with a detailed enlarged view of a screw head, according to an aspect.

FIG. 9 illustrates another example of the lateral (side) view of the spinal column 911 having magnetic core bone screws 900-*a* inserted, with a detailed enlarged view 930 of a screw head 966, according to an aspect. The body 949 of the individual vertebra, the intervertebral disc 954, and the spinal nerve 956 are visible in this view. Again, similar to the discussion when referring to FIG. 4, the repulsion of the magnets 900-*a* inside the magnetic core bone screws 900-*a* may help to relieve pressure from the vertebrae 949 on the spinal nerve 956. As an example, a first screw 900-*a* having a magnet 926-*b* within the screw head 966 may be positioned in a first vertebra 949 such that the magnet's south pole 903 is pointed upwards towards the superior side of the vertebra, and the magnet's north pole 902 is pointed downwards towards the inferior side of the vertebra, as shown in the detailed enlarged view 930. Next, a second screw 900-*a*2 having a magnet 926-*b* within the screw head 966 may be positioned in a second vertebra 949-*a* on the inferior side of the first vertebra 949. The magnet 926-*b* of the second screw 900-*a*2 may be oriented such that the north pole is facing towards the north pole 902 of the first screw 900-*a*, and the south pole is facing away from the first screw 900-*a*.

Figure 10:
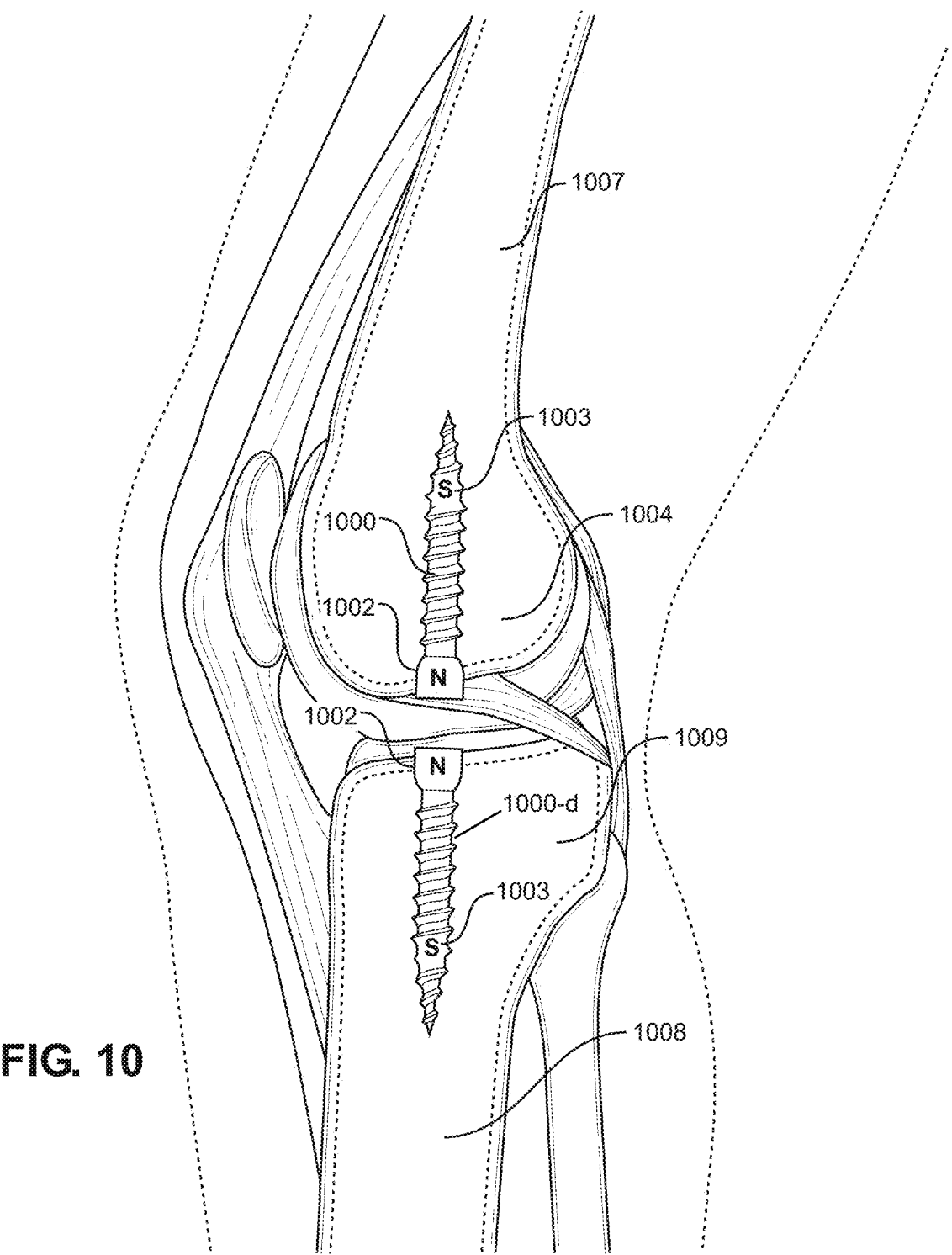
FIG. 10 illustrates the side view of the bones of the leg with inserted magnetic core bone screws, according to an aspect.

FIG. 10 illustrates the side view of the bones of the leg with inserted magnetic core bone screws 1000 and 1000-*d*, according to an aspect. The exemplary view shows an example of magnetic core bone screws 1000 in the tibia 1007 and the femur 1008, with the tibia 1007, medial condyle of the tibia 1004, femur 1008, and the medial epicondyle of the femur 1009 visible. The magnetic core bone screws 1000 may be used in any other suitable bones of the body to acquire the correct anatomical position needed for the patient. As shown as an example, two magnetic core bone screws may be placed across from one another in the tibia and the femur. The north poles 1002 and south poles 1003 of the magnetic core bone screws 1000 may be aligned as shown such that the two bone screws 1000 are repulsed from each other. The exemplary alignment of the first and second magnetic core bone screws may achieve a therapeutic effect or relieve pain or tension in the patient, for example.

Figures 11A, 11B:
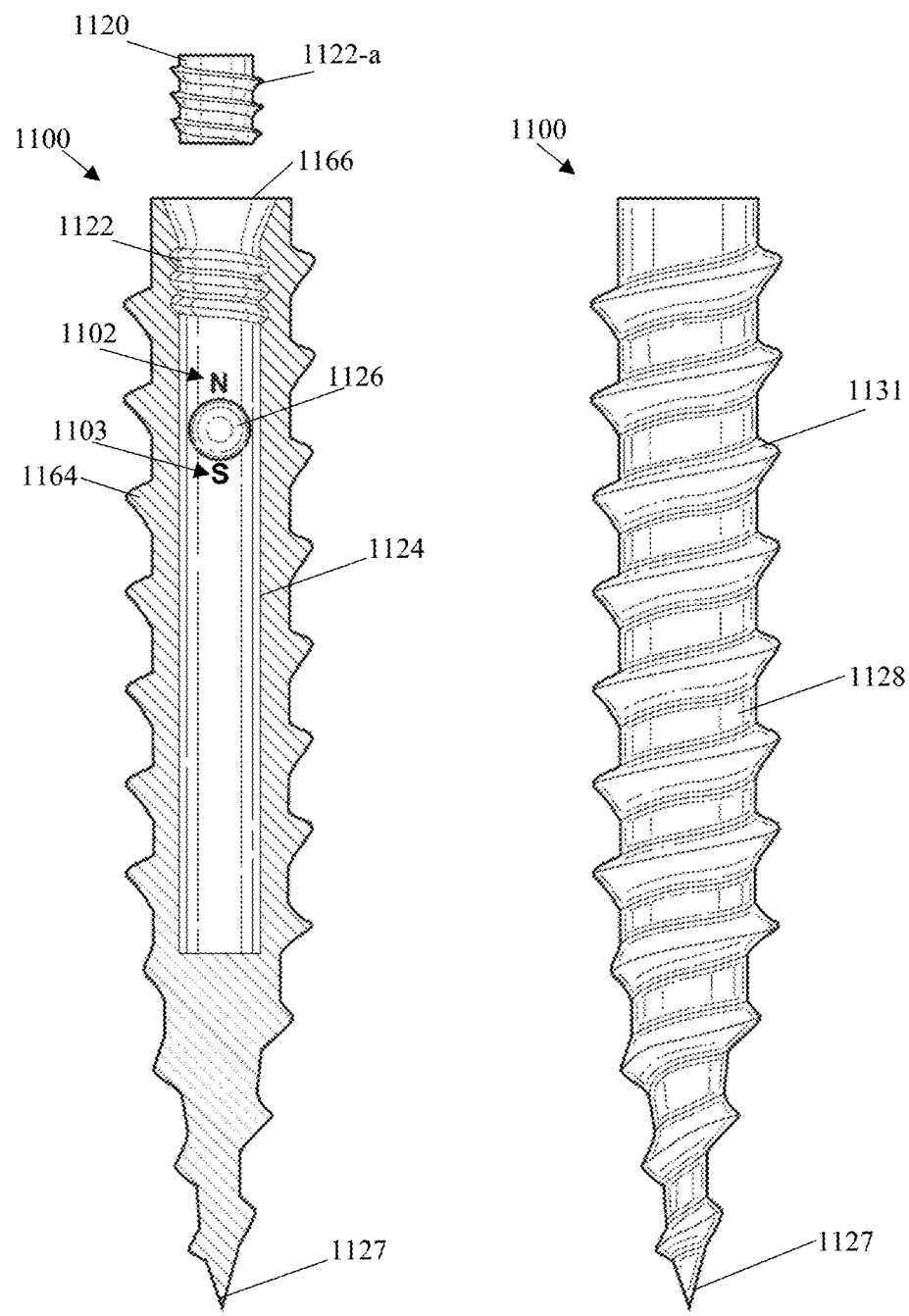
FIGS. 11A-11B illustrate a side sectional view and a side view, respectively, of a magnetic ball core bone screw, according to an aspect.

FIGS. 11A-11B illustrate a side sectional view and a side view, respectively, of a magnetic ball core bone screw ("magnetic ball core bone screw," "magnetic bone screw," "bone screw"), according to an aspect. Bone screws 1100 containing magnetic ball cores may screwed into the vertebrae or other bones of the body with a screwdriver, for example, or any other suitable means. The bone screw 1100 may include a head 166, which may be associated with a screw cap 1120, a shaft 1164, and a tip 1127 at the opposite end of the head 1166 which may be pointed to aid in the drilling and the insertion of the bone screw 1100 into a bone. The shaft 1164 may extend between the head 1166 and the tip 1127. The bone screw may be provided with an inner cavity or chamber 1124 for housing a magnetic ball 1126, which may thus become the magnetic ball core 1126 ("magnetic ball core," "magnetic ball," or "magnet") of the bone screw. The magnet 1126 may, for example, be neodymium, or any other suitable metal. As an example, the magnetic core 1126 may be housed within a chamber 1124 located in the shaft 1164 of the bone screw 1100. The magnetic ball 1126 having a north pole 1102 and a south pole 1103 may be placed in the interior cavity 1124 of the bone screw 1100 as shown in FIG. 1A, such that the magnet is not visible from the exterior of the screw, as shown by FIG. 11B. The exterior casing 1128 of the screw 1100, which may completely surround and encase the magnet 1126, may be constructed from a material not likely or less likely to be rejected by the human body, such as, for example, titanium or ceramic materials. An advantage may be that additional coatings may not be needed on the magnet itself, thus again reducing the risk of rejection of materials by the patient's body. A complete encasing of the magnet 1126 by the exterior casing 1128 may thus reduce the risk to a patient of injury, rejection of implanted materials, or complications following a surgery.

The bone screw 1100 may also be provided with interior threads 1122 at a top end of the screw at the head 1166, and the inner threads 1122 may be threaded or associated with the cap threads of 1122-a of a top screw cap ("top screw cap," "screw cap" or "cap") 1120. The cap 1120 may then seal in the magnet 1126 such that no portion of the magnet is exposed or visible outside of the exterior casing 1128 of bone screw 1100, and the cap may be constructed from the same or similar material as the exterior casing 1128 (e.g., titanium). The cap 1120 may allow for the magnet 1126 to be removably inserted into the bone screw and replaced or placed at a different depth in the interior cavity 1124, as needed, for example. As shown by FIG. 11B, the bone screw 1100 may be provided with exterior threads 1131 on the exterior casing 1128 surface, which may aid a user in screwing, drilling, or inserting the bone screw 1100 into bone.

As discussed similarly when referring to FIG. 2, the screw cap 1120 may be provided with a recess or screw drive, configured to receive any means or tool for driving the bone screw 1100 into a vertebra. As an example, the bone screw may be provided with a recess or screw drive such as, for example, a Phillips head, or any other suitable type of screw drive. The bone screw 1100 may also be constructed with a screw drive such as an Allen's head as an example, or any other suitable type of screw drive, which may be used for receiving a means for driving the screw 1100 into the vertebra. It should be noted that the screw cap 1120 and the screw head 1166 may each independently comprise a recess or screw drive for the removal of the bone screw from the vertebra without the removal of the screw cap, as an example.

The magnetic ball core bone screws 1100 may be used to help correct the curvature of a spine affected by scoliosis and/or to relieve pain or pressure, for example. As examples, the screws may be used to align the curved vertebrae; the magnetic core bone screws 1100 may be placed in several vertebrae in series such that the vertebral column may be brought into a proper or desired alignment. Magnetic core bone screws 1100 may thus be used as a part of a minimally invasive surgical technique. The magnetic ball 1126 shown in FIG. 11A may be placed within the interior cavity 1124, which occupies the length of the shaft 1164, as shown. Furthermore, the magnet 1126 may be free rolling and free spinning within the chamber 1124, such that the magnet may freely rotate and align itself with a magnetic field of a neighboring magnet, and travel along the length of the chamber 1124 to reach any depth needed for continuous correction of scoliosis of the spine. As will be discussed in further detail throughout this disclosure below, the ability of the magnets within the bone screws to freely spin will cause the curved vertebrae of the spine to realign themselves into a straight line running down the spinal column.

During use, after the magnetic bone screw 1100 has been implanted in vertebrae of the spine, the user may experience slight levels of discomfort when, for example, the user moves from a vertical standing position to a horizontal resting position. Because the magnetic ball 1126 is free to move along the interior cavity 1124, temporary changes in the ball's orientation (e.g., due to the force of gravity) may cause shifts in the magnetic field between successive magnetic ball core bone screws, thus causing the slight discomfort during certain user activities. Thus, in an effort to dampen any discomfort the user may experience, the interior cavity 1124 may additionally be provided with a suitable substance or material to slow the motion of the magnetic ball 1126 as it changes orientation. As an example, the interior chamber may be lined with a substance like viscous oil or grease to suitably slow the movement of the ball 1126. Alternatively, balls or cylinders made from materials like polypropylene, polyethylene or moldable foam may be placed within the chamber 1124 on either side of the magnetic ball 1126 to slow the movement of the ball, as an example. As another example, non-magnetic springs could be placed on opposite ends of the chamber 1126 to slow the motion of the magnetic ball, as well. It should be understood that the chosen substance or material should be non-magnetic so as to not interfere with the magnetic ball within the chamber.

The magnetic core bone screws may also be used alone or in tandem with other therapies to align the spine for those that suffer from improper curvature such as that which may occur in scoliosis. For example, another therapy or technique that the magnetic core bone screws may be used with is the attachment or placement of external magnets, which may be strapped into fixed positions outside of the body of the patient or the user, which may assist in further bringing bones which have magnetic core bone screws drilled into them into a proper or desired position or alignment over time.

Another advantage may be that this minimally invasive technique may require no brackets, rods, or other apparatuses to be attached to the bones or vertebrae, thus requiring fewer materials and less potential risk of rejection of the inserted materials in the patient. Brackets for holding a magnet to the bones may also be eliminated from the process, and multiple steps for inserting a magnet into the bone (e.g., predrilling a guide hole) may be reduced only to the one step of screwing the bone screw with an embedded or encased magnet into the bone. Thus, another advantage may be that these surgical procedures may be more efficient than currently known techniques.

The magnetic core bone screws may be constructed to be the size of conventional bone screws as known in the art or may be constructed to be slender enough to fit through the thickness of a hypodermic needle. Thus, another advantage is that the magnet embedded within the bone screw may require no additional coating, being encased completely within the bone screw itself.

Figure 12:
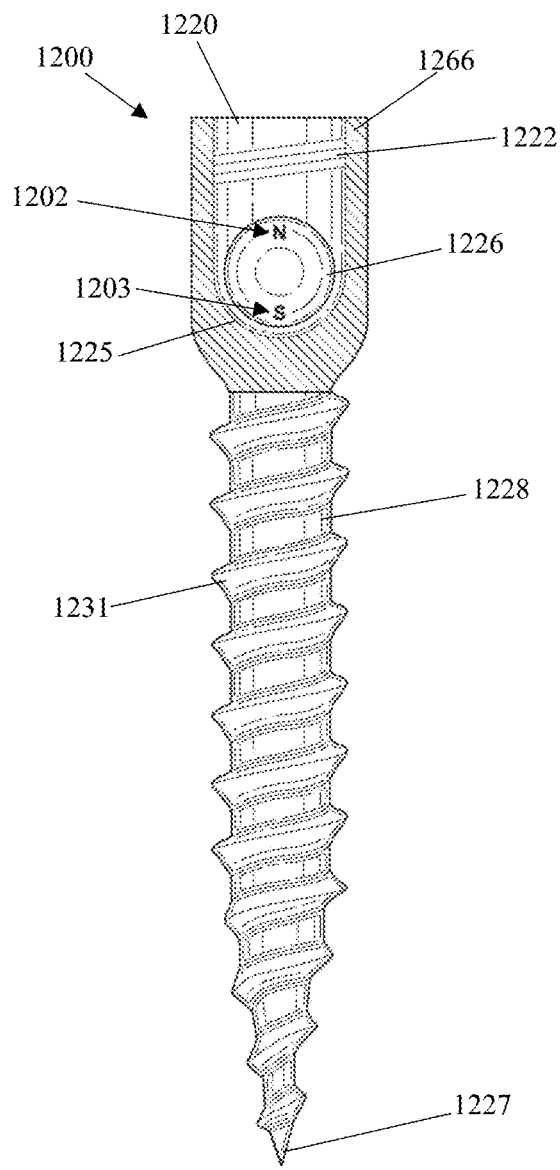
FIG. 12 illustrates a side partially sectional view of another example of the magnetic ball core bone screw, having a magnetic ball placed inside the screw head, according to an aspect.

FIG. 12 illustrates a side partially sectional view of another example of the magnetic ball core bone screw 1200, having a magnetic ball 1226 placed inside the screw head 1266, according to an aspect. As shown in FIG. 12, the magnetic ball core bone screw 1200 may be provided with a spherical cavity 1225 within the head 1266 of the screw 1200. As shown as an example, the magnetic ball 1226 may be placed as a floating magnet within the spherical cavity 1225, allowing the magnet 1226 to freely spin within the cavity 1225. As mentioned previously above, the magnet 1226 may freely spin to align itself with the magnetic field of a neighboring magnet within a neighboring bone screw. As shown, the magnetic ball 1226 may include a north pole 1202 and a south pole 1203. As will be discussed in further detail when referring to FIG. 14, the north pole 1202 of a first magnet may be attracted to the south pole 1203 of a second magnet, which will pull the two magnets toward each other, thus bringing the respective vertebrae into alignment. The screw top 1220 may then be screwed onto the screw head 1266, forming a seal via the threads 1222, such that the magnet 1226 is completely encased within the spherical cavity 1225, as shown as an example. A complete encasing of the magnet 1226 by the screw top 1220 may thus reduce the risk to a patient of injury, rejection of implanted materials, or complications following a surgery.

As shown in FIG. 12, this additional embodiment of the present invention may also be provided with a pointed tip 1227 and exterior threads 1231 wrapping the body of the bone screw 1200. The head 1266 of the screw 1200 may be configured to receive a driver or drill point (e.g., end of a screwdriver or power drill) to drive the screw into bone. As previously discussed above, the tip 1227 and exterior threads 1231 may allow a user to drive and insert the bone screw 1200 into a bone as the screw head 1266 is rotated more easily. As described previously above, the bone screw 1200 may be made from a suitable material such as titanium or ceramic and the magnet 1226 may be made of neodymium, as examples. Manufacturing the bone screw from these materials may reduce the risk of internal infection or the body rejecting the bone screw altogether.

Thus, an advantage of the magnetic core bone screw shown in FIG. 12 is that the magnet may freely spin within the head of the screw, allowing the magnet to align itself within the magnetic field of a neighboring magnet, causing the vertebrae to realign. Another advantage of the secondary embodiment of the bone screw is that the implanting of the bone screw into the body does not require multiple steps, thus reducing the time necessary to perform the procedure. An additional advantage is that the bone screw shown in FIG. 12 may be easily implanted in the body to correct scoliosis of the spine without the need for additional internal rods or mounting apparatuses.

Figure 13:
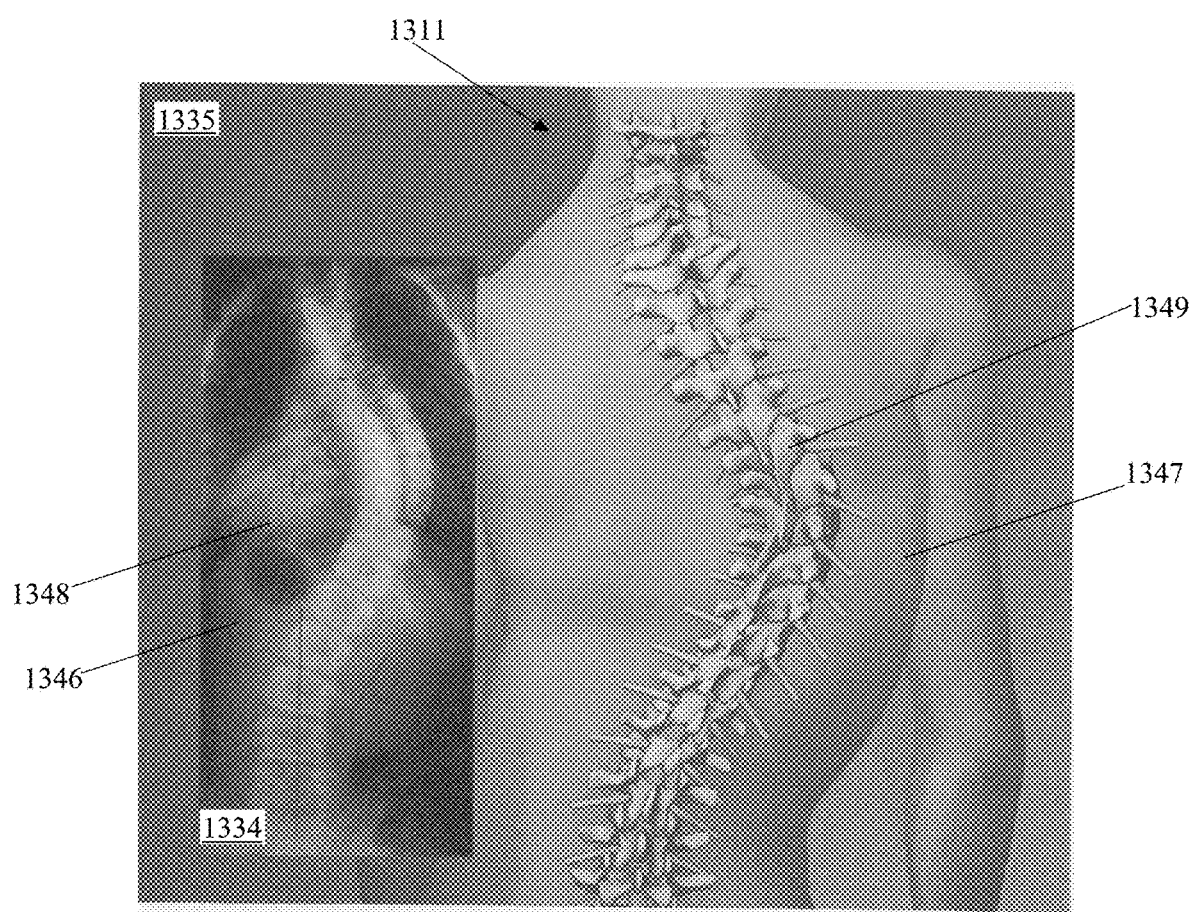
FIG. 13 illustrates a rear view of an X-ray and a 3D model of an exemplary spine with scoliosis, according to an aspect.

FIG. 13 illustrates a rear view of an X-ray 1334 and a 3D model 1335 of an exemplary spine 1311 with scoliosis, according to an aspect. As an example, a patient may be diagnosed with spinal scoliosis by visual inspection or via an X-ray 1334, as shown. As shown in FIG. 13, the curving of the spine 1311 may cause the ribs 1348 to twist and/or cave, which in extreme cases can lead to chest and back pain, as well as shortness of breath. Furthermore, as shown, the curving of the spine 1311 can cause the head of the patient to appear off-balance, and the back 1347 and the hip bone 1346 of the patient to abnormally push outwardly to the side, as well. The bone screw disclosed above and shown in FIGS. 11A-11B, and 12, may be implanted into the curved vertebrae 1349 of the spine 1311 to correct the scoliosis causing the abnormal curvature, as will be discussed in further detail below.

Figure 14:
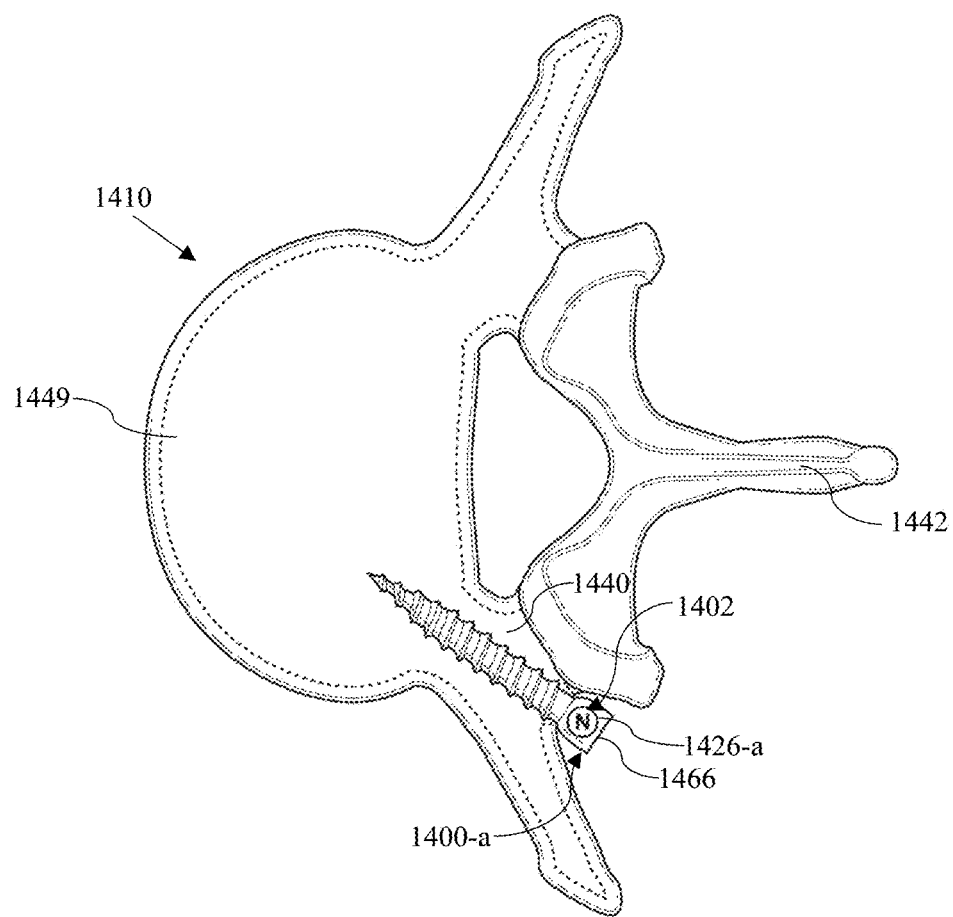
FIG. 14 illustrates a top view of a vertebra with a magnetic ball core bone screw screwed into the interior of the vertebral bone body, according to an aspect.

FIG. 14 illustrates a top view of a vertebra 1410 with a magnetic ball core bone screw 400-*a* screwed into the interior of the vertebral bone body 1449, according to an aspect. The transverse processes 1440 and the spinous process 1442 of the vertebra 1410 are visible in this exemplary view. The magnetic core bone screw 1400-*a* may have the magnetic ball 1426-*a* located in the interior of the head 1466 of the screw 1400-*a*, the north pole 402 of the magnet being pointed towards the superior side of the vertebra 410, as an example. As previously described above, the magnetic ball 1426-*a* may free-floating and can therefore spin freely within the head 1466 of the screw 1400-*a*. Thus, it should be understood that the north pole 1402 and the south pole (not shown) may alternate between being pointed towards or away from the superior side of the vertebra 1410.

In an aspect of the current invention, a method of correcting scoliosis of the spine is provided with the magnetic ball core bone screw disclosed herein above. The method may involve first locating the curved vertebrae of the spine of a diagnosed patient using an X-ray or other medical imaging means, as an example, to determine the location(s) of bone screw insertion within the spinal column. Then, as shown in FIG. 14, a magnetic ball core bone screw may be inserted into each vertebra exhibiting abnormal curvature. A magnetic ball core bone screw may be inserted into the convex (outer) side of the curved vertebra, such that the curved vertebra may be pulled into proper alignment by successive bone screws inserted above and/or below it. As shown as an example, a magnetic core bone screw 1400-*a* may be inserted into the vertebra 1410 just to the left of the spinous process 1442, with the head 1466 of the screw left uninserted or partially uninserted into the bone 1449. Alternatively, the magnetic core bone screw 1400-*b* may be inserted just to the right of the spinous process 1442, should the spinal column be protruding in the opposite direction. A bone screw may be placed into each curved vertebra following this same process. The bone screws may be screwed into each vertebra using any means or tools known in the art, such as a screwdriver or power drill. It should be noted that, preferably, three (3) or more vertebrae may be treated at a time to allow the vertebrae to adjust. Then, the remaining (if any) vertebrae may be treated to adjust and realign those vertebrae with the rest of the spinal column. Once the bone screws have been inserted into each of the identified curved vertebrae, the spinal column may resemble that shown in FIG. 15.

It should be understood that two magnetic ball core bone screws may be inserted into each vertebra, one bone screw on either side of the spinous process 1442. However, this method may be less preferred as a method of correcting scoliosis. Using one bone screw in the vertebrae at a time may be more effective and therefore more preferable, as the insertion of one bone screw into each vertebra is a less invasive surgical method. As such, for the purposes of this application, using one bone screw in the vertebra, as shown in FIG. 14, is thus considered the correct method of correcting scoliosis. Furthermore, as described herein above, inserting the magnetic ball core bone screw on the convex side of the curve(s) may provide the additional advantage of allowing successive vertebrae to attract toward each other at much greater magnitudes than if two magnetic ball core bone screws were inserted into each vertebra, thus further facilitating the correcting of the uneven gap that exists between successive vertebrae in a spine suffering from scoliosis.

As an example, at the apex or peak of each scoliosis curve (the most-curved vertebra) that needs correction, the surgeon may elect to use magnetic ball core bone screws emitting stronger magnetic fields (e.g., magnetic balls having greater strength). At points along the spine that require less correction (minimal curvature), the surgeon may elect to use magnetic ball core bone screws emitting weaker magnetic fields. As such, the required strength of the magnetic ball core bone screw inserted into each respective vertebra can be determined by analyzing the difference in the gaps between a given pair of vertebrae on the right side of the spine and the left side of the spine. As an example, the greater the difference in the gap side to side (i.e., the greater the curvature to either the left or the right), the stronger the magnetic ball of the magnetic ball core bone screw that is to be inserted into that particular vertebra should be. Alternatively, the lesser the difference in the gap side to side (i.e., the lesser the curvature to the left or the right), the weaker the magnetic ball should be, as an example.

Figure 15:
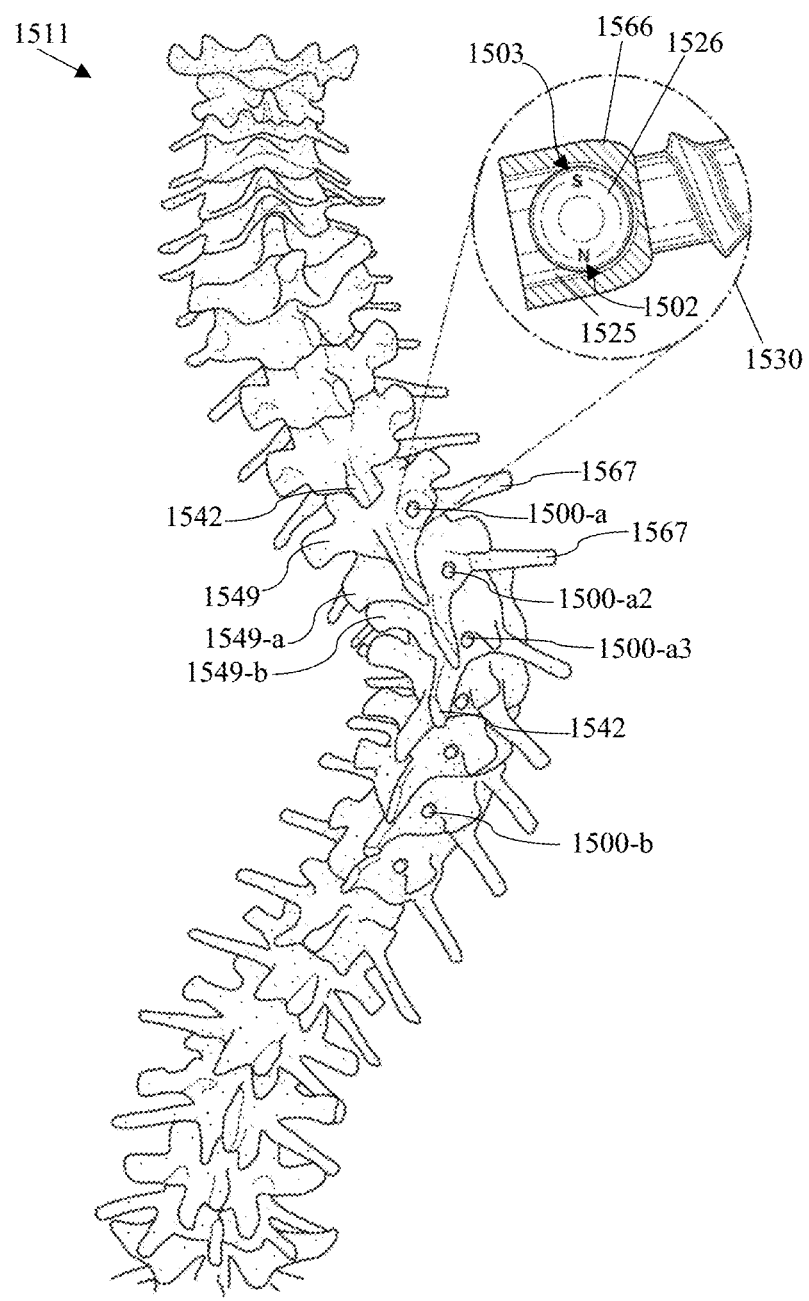
FIG. 15 illustrates a rear view of a spine having scoliosis, with inserted magnetic ball core bone screws and a detailed enlarged view of a screw head 1566, according to an aspect.

FIG. 15 illustrates a rear view of a spine 1511 having scoliosis, with inserted magnetic ball core bone screws 1500-*a*-1500-*a*3 and a detailed enlarged view 1530 of a screw head 1566, according to an aspect. The body 1549 of the individual vertebra, the spinous process 1542, and the transverse process 1567 are visible in this view. Continuing the discussion of the method described when referring to FIG. 14, the attraction of the magnets 1526 inside the magnetic core bone screws 1500-*a*-1500-*a*3 may help adjust the vertebrae 1549-1549-*b* and correct the alignment of the spinal column 1511. Additionally, the slight repulsion of any nonsequential bone screws (e.g., 1500-*a* and 1500-*a*3), may help to relieve pressure from the vertebrae 1549, 1549-*a* on the spinal nerve (not shown). As an example, a first screw 1500-*a* having a free-floating magnet 1526 within the screw head 1566 may be implanted in a first vertebra 1549. Next, a second screw 1500-*a*2 having a magnet within the screw head may be positioned in a second vertebra 1549-*a* on the inferior side of the first vertebra 1549, as shown. Because the magnets 1526 inside each bone screw 1500-*a*, 1500-*a*2 are free to spin, the south pole 1503 of the magnet 1526 in the screw 1500-*a* may rotate and position itself to point toward the north pole of the magnet in the screw 1500-*a*2, as shown as an example in the detailed enlarged view 1530.

As an example, in operation, the freely spinning magnetic balls 1526 within the bone screw heads 1566 will naturally align themselves over time to form a single straight magnetic field running along the spinal column 1511. Due to the attraction of the opposite polarities of the magnetic poles (e.g., 1502 and 1503), the magnets 1526 will pull toward each other, causing the bone screws (e.g., 1500-*a* and 1500-*a*2) to be pulled as well. As the bone screws 1500-*a*, 1500-*a*2 magnetically pull toward each other, the vertebrae 1549, 1549-*a* will be forced to shift and readjust as well. Over time, because the magnets 1526 are free spinning, the bone screws 1500-*a*, 1500-*a*2 will continuously pull toward each other, even as the vertebrae 1549, 1549-*a* shift in position.

As mentioned previously above when referring to FIG. 14, it may be preferable to treat three or more vertebrae at a time. As shown as an example in FIG. 15, more than three bone screws may be used if necessary. In the method of use it should be understood that the most curved vertebrae should be treated first, such as 1549-*a* and 1549-*b* shown in FIG. 15. By inserting the bone screws 1500-*a*2, 1500-*a*3 on the convex side of the curve, as shown, the most curved portions of the spinal column may be pulled into proper alignment. Using the preferred method of treating three or more vertebrae at a time, bone screws 1500-*a*-1500-*a*3 may be implanted into the vertebrae 1549-1549-*b*. Then, after some time has passed and the most curved vertebrae have shifted, additional bone screws may be added, as shown by 1500-*b*, or the existing bone screws may be relocated, such that the magnets 1526 in the magnetic ball core bone screws continue to pull on each other until they align to form a straight magnetic field, resulting in a more fully corrected spinal column.

Thus, an advantage of the disclosed method of correcting scoliosis is that because the magnet within the bone screw is free spinning, the need for precise positioning and orientation of the magnet within the screw may be negated. Another advantage of the method is that the need to implant braces, rods or other mounting apparatuses may be negated. An additional advantage of the method is that because the vertebrae are not fused together via spinal fusion, the patient may not experience permanent stiffness. Another advantage of the disclosed method is that, due to the minimally invasive surgical technique utilized, the patient may experience less scarring.

It should be understood that a combination of the embodiments of bone screws disclosed herein may need to be used.

As an example, if correction in the ventral dorsal direction of the curvature of the spine is needed, it may be necessary or advantageous for the magnetic core bone screws to be implanted into the vertebrae at different depths depending on, for example, the angle of curvature of the spine. Alternatively, the magnetic ball may be positioned at a preselected fixed depth within the shaft of the bone screw. As such, a first bone screw inserted into a vertebra may be of the type shown in FIG. 12, and a second bone screw inserted into another vertebra may be of the type shown in FIGS. 11A-11B, with the magnet placed at a predetermined depth within the interior cavity of the bone screw, as an example. The magnetic ball within the shaft cavity may then be free to move back and forth within the cavity of the bone screw to align itself with neighboring magnetic balls implanted in neighboring vertebrae, as an example. Thus, an advantage is that because the magnetic ball is free to move back and forth within the shaft of the screw, the correct natural ventral dorsal curve of the spine may be maintained while still correcting the scoliosis curve of the vertebral spine from the lateral to the medial direction. Another advantage is the increase in range of the depth that a surgeon may implant the magnetic core bone screw into the vertebra, since the free maneuverability of the magnetic ball within the bone screw may maintain the correct ventral dorsal curve of the spine during scoliosis correction.

Figure 16A:
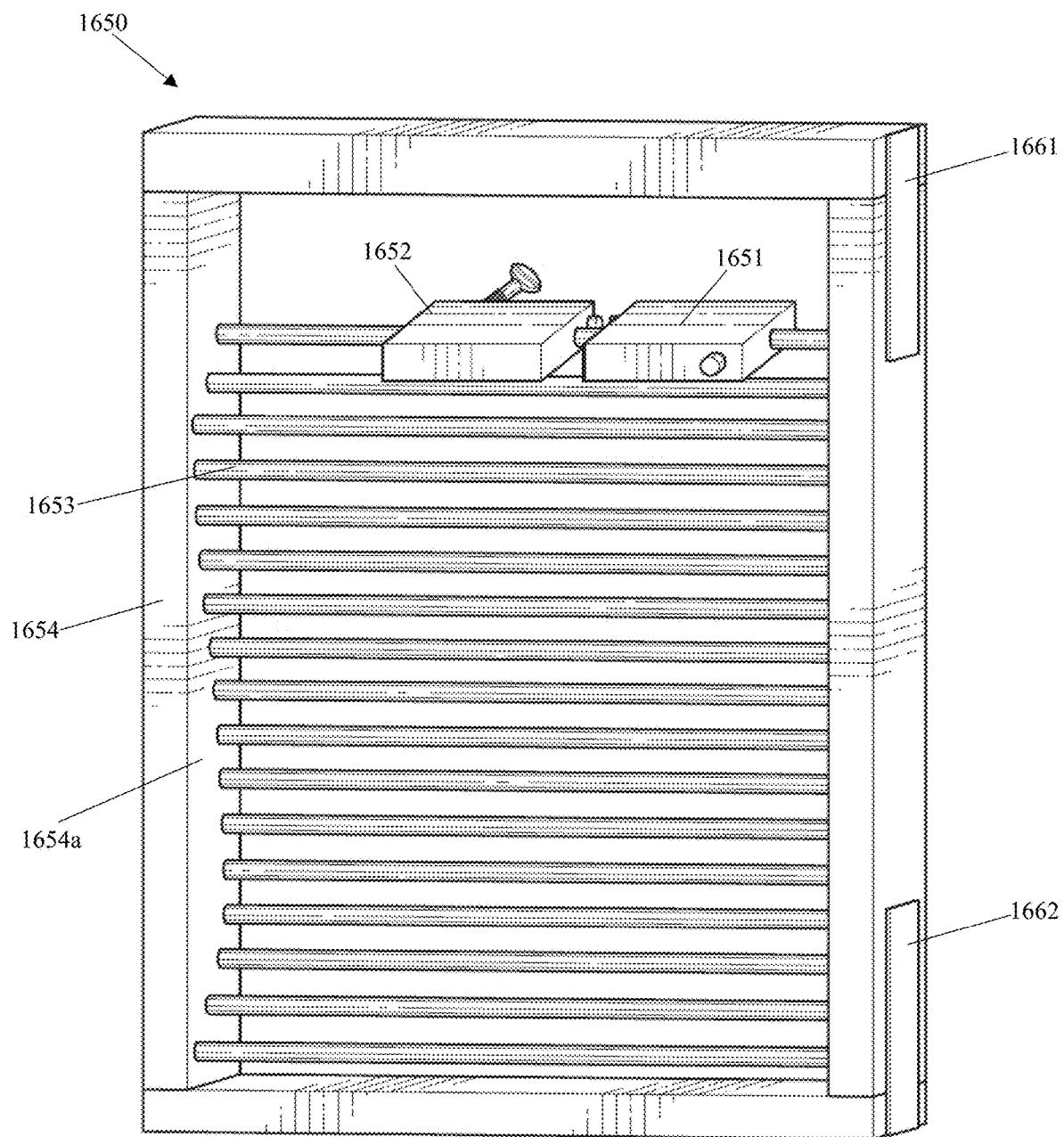
FIGS. 16A-16B illustrate a perspective view and a front view, respectively, of a scoliosis correction abacus, according to an aspect.
Figure 16B:
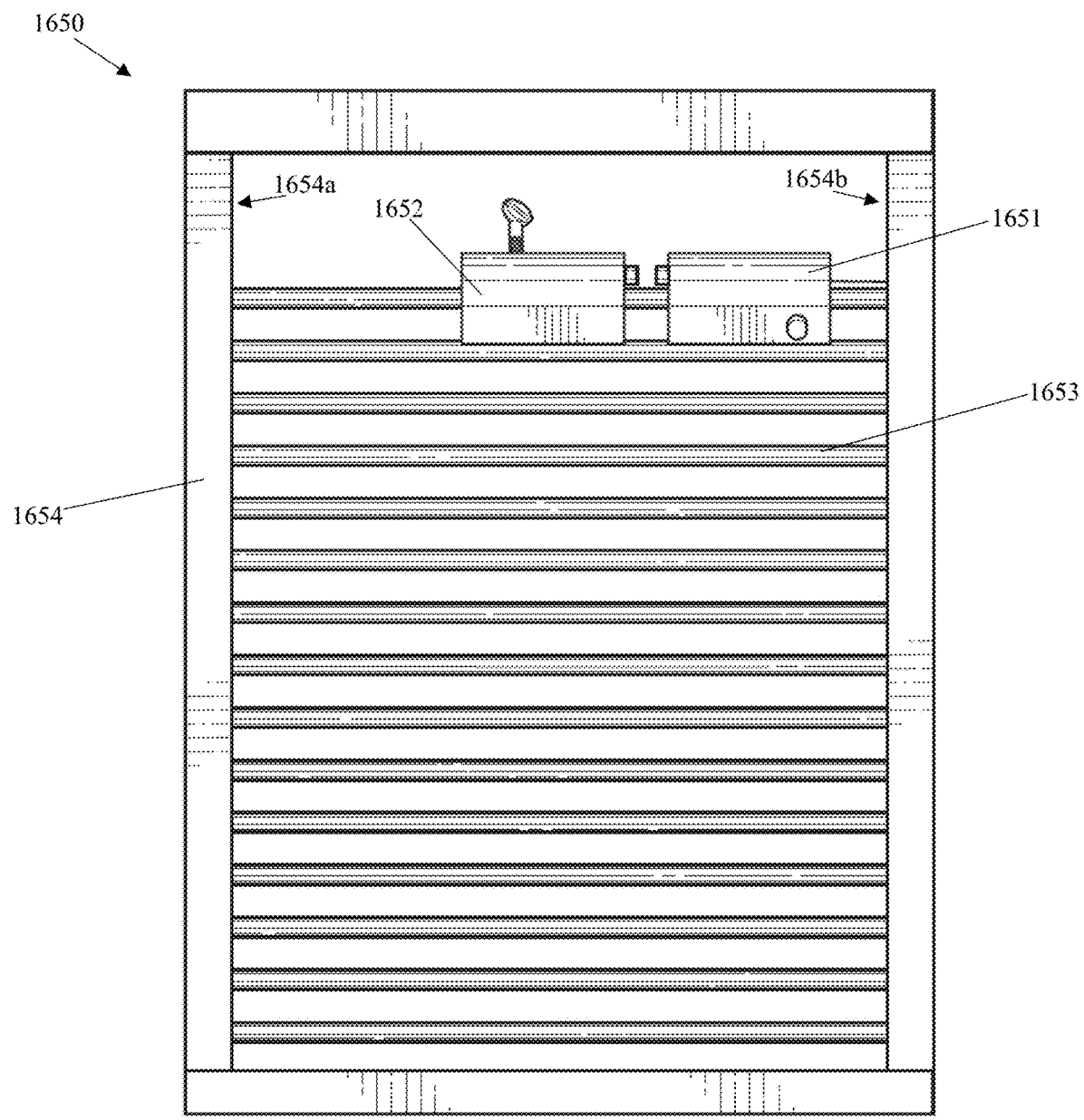

FIGS. 16A-16B illustrate a perspective view and a front view, respectively, of a scoliosis correction abacus 1650, according to an aspect. As described throughout this disclosure above, magnetic ball core bone screws may be implanted into vertebrae to correct the abnormal curvature of a spine suffering from scoliosis. The magnets within the screws attract and/or repel each other, causing the individual vertebrae to shift until they are properly aligned in a single vertical line. In extreme cases of scoliosis, particularly where the bone screws alone cannot cause complete realignment of the spine, the scoliosis correction abacus 1650 could be used in conjunction with the already implanted bone screws. In another aspect of the present invention, a system for correcting scoliosis of the spine is provided, wherein the system comprises magnetic ball core bone screws and the scoliosis correction abacus 1650. As described previously herein, it may be preferred to treat the most curved vertebrae first. As such, employing the correction abacus 1650 to help correct scoliosis initially during the treatment process, as will be described in detail below, may more effectively correct the scoliosis in the long run.

As shown in FIGS. 16A-16B, the correction abacus 1650 may be provided with a frame 1654, as an example. Although the frame 1654 of the correction abacus 1650 is depicted as having a rectangular shape, it should be understood that the abacus could be designed to be circular, octagonal, or any other feasible shape. As shown, the correction abacus 1650 may be provided with a plurality of rods 1653. As shown as an example, each rod 1653 may extend horizontally from a first interior wall 1654*a* of the frame 1654 to a second interior wall 1654*b*, such that the rods 1653 are secured within the frame 1654. The correction abacus 1650 may also be provided with a plurality of magnetic riders 1651, 1652. While only one pair of riders 1651, 1652 is shown in FIGS. 16A-16B, it should be understood that multiple pairs of riders may need to be used within the abacus 1650, with each rod 1653 comprising no more than one pair of riders 1651, 1652 (see e.g., FIG. 18).

As an example, during use, the scoliosis correction abacus 1650 could be worn by a patient requiring further correction of the spine. The scoliosis correction abacus 1650 could be configured to attach to the patient's back by any suitable means. As shown as an example in FIG. 16A, the correction abacus 1650 may be provided with shoulder straps 1661 and waist straps 1662 that may be extended outwardly from the abacus 1650 and attached around the user's shoulders and waist, respectively. It should be understood that other attachment means may be used, such as buckles, chords, or having the abacus placed within a backpack, for example. As shown in FIGS. 16A-16B, the scoliosis correction abacus 1650 should be oriented to face the back of the patient, such that the front of each magnetic rider 1651, 1652 faces toward the patient's back. The functionality of the correction abacus 1650 will be discussed in further detail when referring to FIG. 18.

Figure 17:
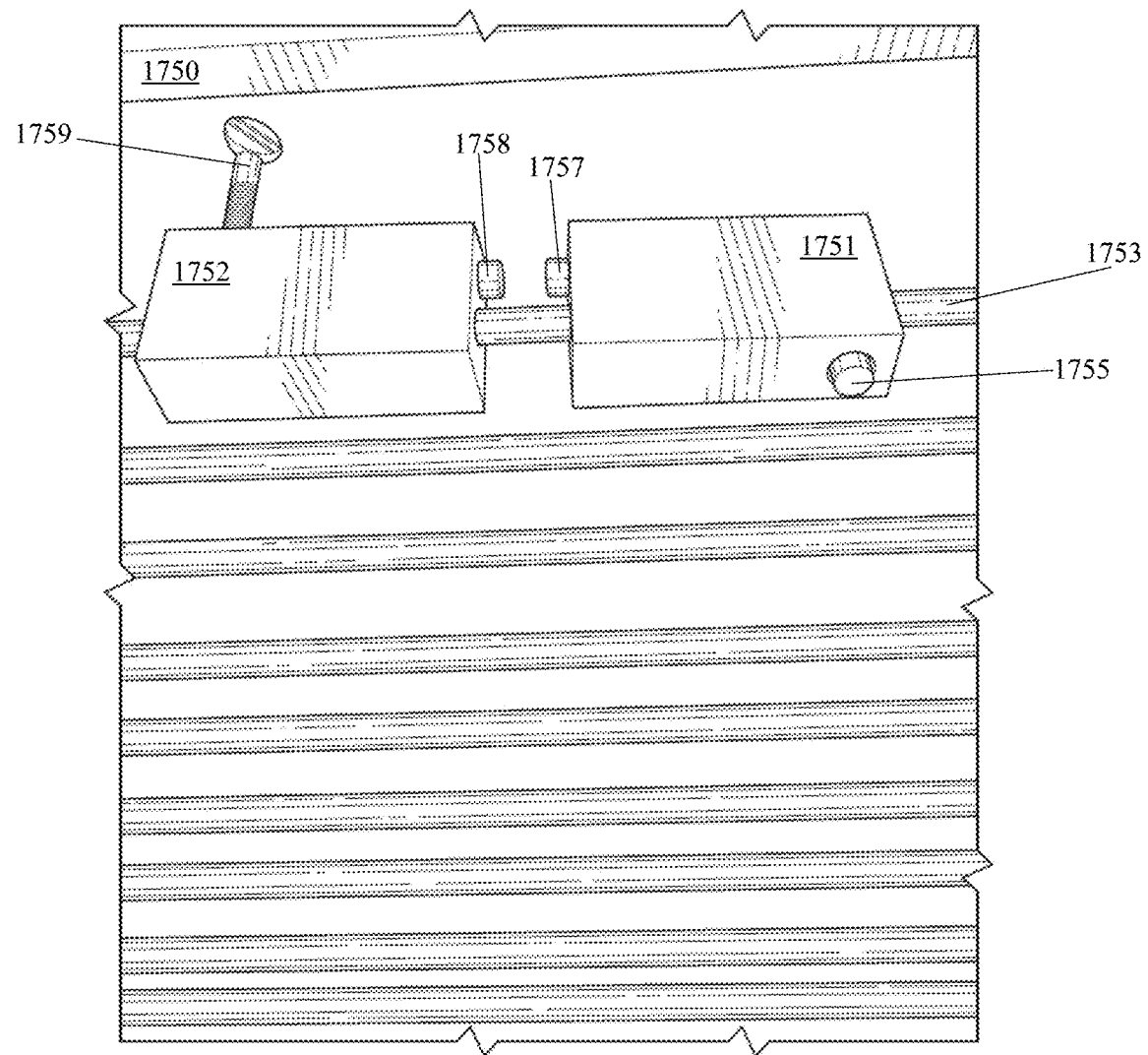
FIG. 17 illustrates a front perspective view of the magnetic riders 1651, 1652 shown in FIGS. 16A-16B, according to an aspect.

FIG. 17 illustrates a front perspective view of the magnetic riders 1651, 1652 shown in FIGS. 16A-16B, according to an aspect. As discussed previously above, the rods of the correction abacus 1750 may be provided with a pair of magnetic riders. Each pair of magnetic riders may comprise a fixed magnetic rider ("fixed magnetic rider," "fixed rider") 1752 and a free magnetic rider ("free magnetic rider," "free rider," "free-moving rider") 1751, as shown. The fixed rider 1752 may be provided with a locking screw 1759, to secure the rider 1752 to the rod 1753, and an attracting magnet 1758, as an example. The free rider 1751 may comprise a set of two magnets 1755, 1757, as shown. The front-facing magnet 1755 may face toward a patient's back when the correction abacus is worn, as an example, such that the magnet 1755 may align with a magnetic bone screw in the patient's spine. The side-facing magnet 1757 may point toward the fixed rider 1752, such that the attracting magnet 1758 may magnetically pull on the side-facing magnet 1757 of the free-moving rider 1751, as an example. It should be understood that each pair of riders 1751, 1752 provided on the rods 1753 may comprise the exemplary components described herein above.

It should be noted that each magnetic rider of the pair of magnetic riders 1751, 1752 may be adapted to be removably associated with the plurality of rods. As an example, the fixed rider 1752 and the free rider 1751 may be configured to be removed from a first rod (via a latching or cuffing means, for example) and may be placed and secured onto a second rod, as needed. Because the number of pairs of magnetic riders 1751, 1752 should correspond to the number of bone screws implanted in the user's vertebrae, it would thus be advantageous for the magnetic riders 1751, 1752 to be easily movable among the plurality of rods.

It should be understood that, according to the proper method of use of the scoliosis correction abacus, only one front-facing magnet 1755 should face and align with a magnetic ball core bone screw implanted in a vertebra. As an example, having more than one magnet 1755 face toward a given magnetic core bone screw in a vertebra may cause the vertebra to shift in the wrong direction or not at all. Furthermore, as described previously when referring to FIG. 14, only one magnetic ball core bone screw should be inserted into each vertebra needing realignment. Accordingly, only one front-facing magnet 1755 should point toward a magnetic ball core bone screw, in the applicable vertebrae.

Figure 18:
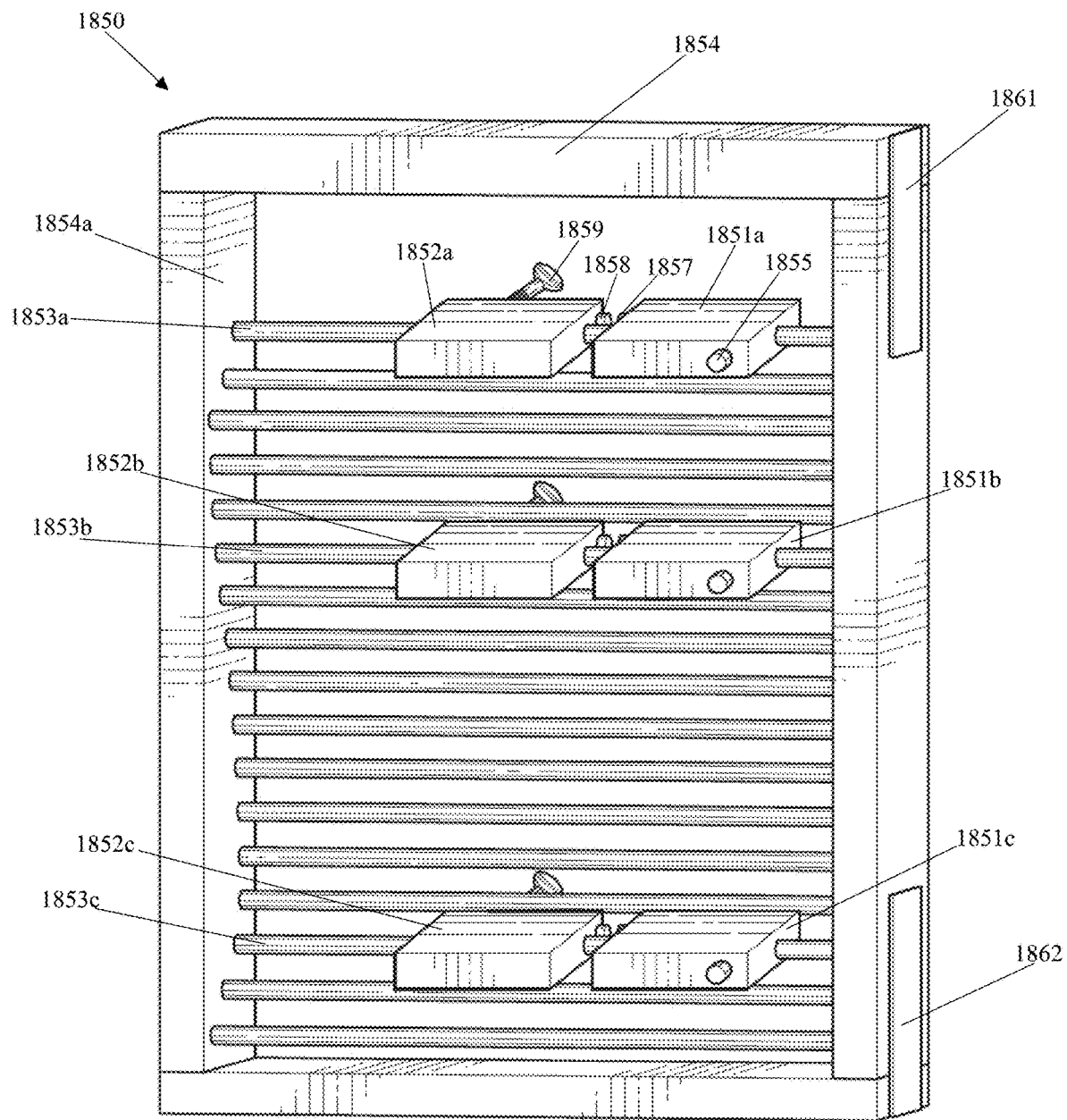
FIG. 18 illustrates a perspective view of a scoliosis correction abacus having multiple pairs of magnetic riders, according to an aspect.

FIG. 18 illustrates a perspective view of a scoliosis correction abacus having multiple pairs of magnetic riders, according to an aspect. As discussed previously when referring to FIGS. 16A-16B, the correction abacus 1850 may be provided with a plurality of rods 1853 that extend horizontally across the interior walls of the frame 1854. As shown in FIG. 18, each rod 1853 may be placed at a different position on the interior walls of the frame 1854, such that the plurality of rods is arranged in a staggered formation. As an example, a top rod 1853a may be positioned in the wall 1854a at a point closest to the rear of the abacus 1850. A second rod 1853b may be positioned in the wall 1854a at a point farther to the left (i.e., between the front and the rear of the abacus) of the top rod 1853a. A bottom rod 1853c, as shown, may be positioned at a point in the inner wall 1854a between the other two rods 1853a and 1853b. Thus, the arrangement of the rods 1853 in the wall 1854a may resemble the natural curvature of the spine (when viewing the spine from the side), as shown.

As shown in FIG. 18, the staggering of the rods 1853 such that to resemble the natural curvature of the spine allows each of the riders 1852, 1851 to be positioned at an equal distance from a bone screw implanted in the spinal column. Thus, the correction abacus 1850 may be placed onto a user's back via the straps 1861, 1862, such that each rider 1852, 1851 may pull on a magnetic ball in a bone screw in the spine with relatively the same magnitude and direction. As will be discussed in detail below, the rods 1853 may be provided with a pair of magnetic riders 1851, 1852 to correspond with a bone screw that may be implanted in each vertebra of the spine.

As described above when referring to FIGS. 16A-16B, the correction abacus may be used in conjunction with the magnetic ball core bone screws to further correct scoliosis of the spine. In continuation of the method described previously above, a patient suffering from a severe case of scoliosis may wear the correction abacus on his or her back, as an example. As mentioned previously in this disclosure, it may be preferable to treat and correct the curvature of three vertebrae or more at a time. Per the method, let the patient have three bone screws implanted into three vertebrae, such that one bone screw is implanted in each of the three vertebrae, as an example. Accordingly, three pairs of magnetic riders 1851, 1852 may be provided in the abacus 1850, such that one pair of riders 1851, 1852 is provided on three rods 1853a, 1853b, 1853c. The placement of the riders 1851, 1852 on the rods should correspond to the position of each bone screw implanted in the patient's spine, such that a first pair of riders on a top rod 1853a aligns vertically and horizontally with a first bone screw in a top-most vertebra (e.g., 1549 in FIG. 15).

As an example, the free rider 1851a may be aligned horizontally along the rod 1853a to position the front-facing magnet 1855 in front of the bone screw in the patient's vertebra. The fixed rider 1852a may then be positioned along the rod 1853a and secured (via the locking screw 1859) at a predetermined distance away from the free rider 1851a. The positioning of the fixed rider 1852a away from the free rider 1851a should correspond to the desired alignment of the spine. In other words, the greater the curve of the spine the farther to the right or the left the fixed rider should be positioned, depending on the desired direction of vertebrae movement. It should be understood that the placement of the fixed rider away from the free rider should always be kept within a suitable range such that to allow the attracting magnet and the side-facing magnet to continuously react.

Per the example above, the three pairs of free riders 1851a-1851c may be aligned with the three bone screws in the patient's spine. During use, the singular front-facing magnet 1855 of each free rider 1851a-1851c may magnetically pull on the magnetic balls of each bone screw. Each fixed rider 1852a-1852c may be positioned and screwed onto the rods 1853a-1853c, respectively, beside each free rider 1851a-1851c and opposite the direction of curvature of the scoliosis. In other words, as an example, if the spine curves/protrudes to the right (as shown in FIG. 15), the fixed riders should be positioned, when the fixed riders are facing toward the user's back, to the left of the free magnetic riders. While the singular front-facing magnet 1855 per free rider 1851*a*-1851*c* pull on each magnet (inside each bone screw) implanted within each vertebra needing realignment in the spine, the side-facing magnets 1857 are simultaneously pulled on by the attracting magnets 1858 of the fixed riders 1852*a*-1852*c*. The fixed riders 1852*a*-1852*c* thus pull on the free riders 1851*a*-1852*c*, respectively, which all pull on the bone screws in the vertebrae of the spine, which may cause each vertebra to shift and come into proper alignment over time. Thus, the correction abacus may efficiently function with the magnetic core bone screws as a scoliosis correction system.

Thus, an advantage of the scoliosis correction system is that the magnetic ball core bone screws may be used with or without the correction abacus to realign the spinal column. Another advantage is that the correction abacus may be conveniently and easily worn by the patient. An additional advantage is that the correction abacus may be made from readily available materials and is therefore cost-effective. Another advantage is that the correction abacus may help correct the curvature of the spine without the need for additional surgery.

The magnets 1855, 1857, 1858 of the magnetic riders may be made of neodymium or any other suitable magnetic metal to react with the magnetic balls of the bone screws. The correction abacus components may be made from any durable, lightweight material (e.g., wood, plastic, aluminum). Additionally, the frame of the abacus may be made of or coated with rubber, foam, or some other material to allow the patient to comfortably wear the abacus during sleep, as an example. While a locking screw is depicted, any suitable or equivalent means (e.g., pin, bolt, thread system) may be used to secure the fixed rider to the rod. Additionally, while the rods are depicted as being circular rods, they may be configured to be rectangular, octagonal, triangular or any other suitable shape. The magnetic riders, though depicted as rectangular blocks, may be designed to be circular or any other suitable shape. It should also be understood that, although the fixed rider is depicted as being positioned to the left of the free rider (front view), the fixed rider may be placed to the right of the free rider as needed, depending on the curvature of the scoliosis.

Figure 19:
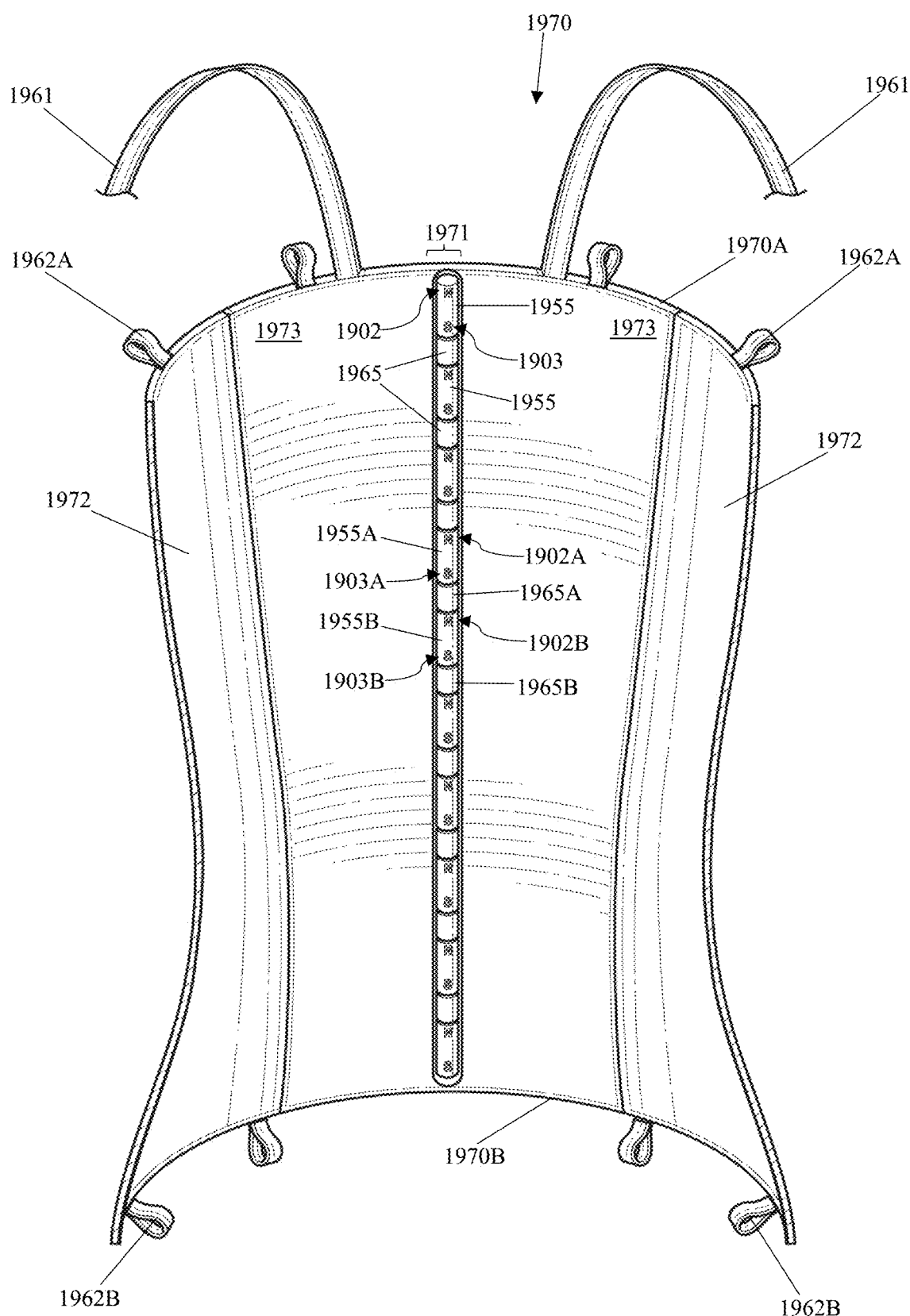
FIG. 19 illustrates a front perspective, sectional view of another example of the scoliosis correction abacus, implemented as a flexible magnetic girdle, according to an aspect.

FIG. 19 illustrates a front perspective, sectional view of another example of the scoliosis correction abacus 1850, implemented as a flexible magnetic girdle 1970, according to an aspect. As shown in FIG. 19, the flexible magnetic girdle ("flexible magnetic girdle," "flexible magnetic hose girdle," "magnetic hose girdle") 1970 may comprise a central girdle body ("central girdle body," "girdle body," "central girdle portion," "stretchable body") 1972 intended to be worn on the torso of the user, which may characterize the magnetic hose girdle 1970 as a simpler, more easily implementable version of the correction abacus 1650 shown in FIGS. 16A-16B, for example. As shown, the magnetic hose girdle may be provided with a flexible hose ("flexible hose," "magnetic hose") 1971 having a plurality of magnetic cylinders ("magnetic cylinders," "magnets") 1955 disposed within and extending the length of the flexible hose 1971. The magnets 1955 may, for example, be constructed from neodymium, or any other suitable material. As will be discussed in more detail below, the flexible hose 1971 may line the center rear of the magnetic hose girdle 1970, such that the magnets within the flexible hose 1971 may magnetically pull on magnetic ball core bone screws implanted in vertebrae of the spine (e.g., 1500-*a* in FIG. 15). The flexible hose 1971 may be constructed of rubber or plastic, for example, to enable the user to comfortably bend over front to back and side to side, while still maintaining the hose 1971 in a straight line down the center rear of the magnetic hose girdle 1970. Furthermore, the flexible hose 1971 may be transparent, as shown, such that to enable the user or a surgeon/physician to ensure the magnetic cylinders 1955 within the magnetic hose 1971 are functioning properly.

As shown, the girdle body 1972 may be made from a stretchy, flexible material 1972 and may comprise a rear reinforcement portion 1973 to provide structural support for the magnetic hose 1971. As an example, the stretchy, flexible material may be made from a nylon spandex blend (e.g., power knit) or any other typically used girdle fabric. The stretchable, flexible material may allow the magnetic hose girdle 1970 to fit snugly and comfortably over the user's torso, such that the flexible hose 1971 having the magnetic cylinders 1955 may be kept closer to the spine, as an example, when worn by the user. The rear reinforcement portion 1973 may be made from leather or a similar material, for example, to provide the magnetic hose 1971 with improved structural integrity and attachment support.

As shown in FIG. 19, the top 1970A of the magnetic hose girdle 1970 may comprise a set of shoulder straps 1961 to help secure the girdle 1970 to the user's body, and to help prevent the girdle 1970 from sliding too low on the user's torso, for example. The shoulder straps 1961 may be made from the same material as the girdle (e.g., leather, power knit) or any other suitable material, for example. The magnetic hose girdle 1970 may also be provided with sets of top 1962A and bottom 1962B belt loops, as shown, to allow a belt (not shown) or other fastening means to be inserted through the belt loops 1962A, 1962B such that to further secure the girdle 1970 to the user's body, as an example. The belt loops 1962A, 1962B may be made from the same material as the girdle (e.g., leather, power knit) or other suitably strong material so as to support a belt or other fastening means, as described above. Thus, an advantage is that the magnetic hose may comfortably be kept in close proximity to the spine having scoliosis, such that to enable the curved vertebrae having magnetic core bone screws to be shifted into proper alignment.

As mentioned previously above, the flexible hose 1971 may be provided with a plurality of magnetic cylinders 1955 disposed vertically within the hose 1971, as an example. As shown in FIG. 19, the magnetic cylinders 1955 may be disposed within the hose 1971 such that the polarities of the magnetic cylinders 1955 are arranged north 1902 to south 1903. It should be understood that the magnetic polarities may also be arranged south to north, alternatively. However, the polarity of each magnetic cylinder 1955 disposed in the flexible hose 1971 should be identical (e.g., each magnetic cylinder is oriented north to south), such that the magnetic cylinders 1955 create their own strong magnetic field. As an example, a first magnetic cylinder 1955A oriented north 1902A to south 1903A within the flexible hose 1971 may attract a second magnetic cylinder 1955B also oriented north 1902B to south 1903B, since the opposite poles (north 1902B and south 1903A) of the first 1955A and the second 1955B magnetic cylinders are pointed toward each other, as shown. Each pair of magnetic cylinders 1955 within the hose 1971 may attract in this way, such that magnetic field lines continuously run between each north and south pole, forming a continuous magnetic field running the length of the hose 1971, as an example.

As shown in FIG. 19, the flexible hose 1971 is oriented vertically and affixed centrally within the girdle body 1972 such that the flexible hose 1971 can run straight down the center midline of the user's back. Thus, the magnetic balls (e.g., 1526 in FIG. 15) of the magnetic ball core bone screws implanted in the user's spine (as shown in FIG. 15) may freely orient themselves within the continuous magnetic field of the magnetic girdle 1970. As similarly described above when referring to FIG. 18, the magnetic ball core bone screw implanted in the user's spine may be either of the embodiments shown in FIGS. 11A-12, as an example. For example, when the magnetic girdle is worn, a magnetic ball disposed within the head (e.g., 1225) of a bone screw may rotate itself, such that its north and/or south poles attract toward the north and/or south poles of a magnetic cylinder of the plurality of magnetic cylinders. Additionally, for example, a magnetic ball disposed within the shaft of a bone screw may rotate and travel along the shaft cavity (e.g., 1124) and then orient its north and/or south poles to attract toward the north and/or south poles of one of the plurality of magnetic cylinders. Thus, when the magnetic girdle is worn by the user, the bone screws (e.g., 1100, 1200) are pulled by the magnetic cylinders 1955, which may cause, over time, the vertebrae to shift into a straight line in the medial to lateral direction.

As shown in FIG. 19, the flexible hose 1971 may also be provided with divider pellets ("divider pellets," "dividers") 1965 positioned in between each pair of magnetic cylinders 1955. As an example, the divider pellets 1965A may be manufactured from a magnetically transparent material like plastic, such that to ensure that each pair of magnetic cylinders (e.g., 1955A and 1955B) may still attract. As shown, the divider pellets 1965 may be used to maintain space and flexibility between pairs of magnetic cylinders 1955 within the hose 1971, such that enough spacing is provided to enable a magnetic cylinder 1955A to spatially align with a particular magnetic ball core bone screw in a vertebra (e.g., 1500-*a2* in FIG. 15). The magnetic cylinders 1955 should be narrow enough in girth so as to slide easily down the flexible hose 1971, but wide enough so as to maintain separation via the divider pellets 1965. As an example, if each magnetic cylinder is 2 cm in length and 2 cm in diameter, and if each divider pellet is 1 cm in length and diameter, then ten magnetic cylinders 1955 may fit adequately within a 30 cm flexible hose having a 2.5 cm inner diameter. As should be understood, the chosen length of the hose 1971, and therefore the numbers and sizes of the magnets 1955 and divider pellets 1965, may depend on the height and/or age of the user (i.e., length of the user's spine). Additionally, larger magnetic cylinders could be utilized to strengthen the magnetic field of the flexible hose, for example.

As mentioned previously above, the flexible nature of the magnetic hose 1971 may enable the user to comfortably bend over front to back and side to side, as an example. The placement of the divider pellets 1965 between adjacent magnets 1955 may further contribute to the flexible nature of the magnetic hose 1971. As an example, using a singular, lengthy magnet within the magnetic hose 1971, rather than the plurality of separated magnetic cylinders, would restrict any normal movement of the spine (e.g., bending). Similarly, allowing the plurality of magnets to make direct contact with each other (e.g., touching of north pole 1902B and south pole 1903A) would hinder any natural bending or stretching while the magnetic girdle 1970 is worn, for example. Thus, an advantage of using divider pellets is that the magnetic hose girdle may allow a user to naturally bend over and/or stretch to the side, while maintaining magnetic attraction between the plurality of magnets and the bone screws implanted in the spine.

It should be understood that the divider pellets 1965 may be any suitable shape, such as cylindrical, spherical, rectangular, triangular, so as to maintain separation between a pair of magnets (e.g., 1955A and 1955B). It should also be understood that the magnetic cylinders may be any other suitably shaped magnets as well, such as spherical, such that to create a continuous magnetic field within the flexible hose. Additionally, although divider pellets are depicted in FIG. 19 and described herein as maintaining separation between pairs of magnets, other suitable means may be employed to achieve the separation and retain flexibility. As an example, the flexible hose may be provided with physical preset grooves and/or barriers within the hose to lock the magnets into place, and thus create spatial separation between pairs of magnets. Furthermore, should the user suffer from a severe case of scoliosis, magnetic cylinders of greater magnetic field strength may be employed to provide a stronger pull on the magnetic core bone screws implanted in the user's spine.

Thus, an advantage is that the magnetic hose girdle may be conveniently and easily worn by the user and later removed, as needed. An additional advantage is that the magnetic hose girdle may be made from readily available materials and is therefore cost-effective. Another advantage is that the magnetic hose girdle may help correct the curvature of a spine having scoliosis without the need for additional surgery.

As an example, the magnetic hose girdle 1970 disclosed herein above may be used in tandem with an exterior scoliosis brace. As described previously above, the magnetic hose girdle may be provided with the sets of top 1962A and bottom 1962B belt loops for further securing the girdle 1970 to the user. If desired, the magnetic hose girdle 1970 may be worn underneath or incorporated with a rigid scoliosis brace (not shown), which may be provided with Velcro® straps lining the top and bottom of the rigid brace, for example. The belts inserted into the top 1962A and bottom 1962B belt loops may have corresponding openings for attachment of the rigid brace Velcro® straps, which may unite the girdle 1970 with the rigid brace. As an example, the rigid brace may be a lightweight 3D-printed back brace, a Boston Brace, a Charleston Bending Brace, or a Providence Brace, among others. The rigid brace should be manufactured or chosen such that to allow space within the brace for the magnetic hose girdle 1970 to adequately fit, as an example. As is known in the art, rigid scoliosis braces are designed to push against the abnormal curvature of the spine, so as to facilitate correction of the curved vertebrae (e.g., 1549-*b* in FIG. 15). This pushing against the abnormal curvature would bring the magnetic ball core bone screws implanted in the spine closer to the magnetic cylinders (1955) of the magnetic hose in the magnetic hose girdle 1970. Thus, utilization of a rigid scoliosis brace may facilitate enhanced and speedier scoliosis correction since the attractive forces between the magnetic ball core bone screws and the magnetic cylinders 1955 may be heightened due to the closer physical proximity of the spine to the magnetic hose 1971.

It should be understood that while a brace may be utilized to enhance scoliosis correction, utilizing the brace is not necessarily preferred as a method of correcting scoliosis. As described herein above, the magnetic hose girdle 1970 or the traditional correction abacus 1850 may function independently to facilitate proper spinal alignment. A user may choose, or a physician/surgeon may recommend, using a rigid scoliosis brace in tandem with the magnetic hose girdle in, for example, cases of severe scoliosis. As such, the magnetic hose girdle may be worn during the day and the rigid brace may be added over the girdle at night for use while the user sleeps, for example. Thus, an advantage of using a rigid scoliosis brace with the magnetic hose girdle is the enhanced correcting of scoliosis of the spine without the need for additional surgery.

It should be noted that the magnetic girdle may be adapted to alternatively have frontal straps, rather than a continuous stretchable body surrounding the user's entire torso. As such, the frontal straps may extend horizontally across the sides of the stretchable body, such that the frontal straps can be tightened as needed across the front of the user's torso when worn, as an example.

As one of ordinary skills in the art may recognize, magnetic core bone screws 1100, 1200 may prove to have a myriad of uses in addition to those described herein above. As an example, the magnetic core bone screws disclosed herein may be adapted to form skull screws for attaching prosthetics to the skull. The magnetic core skull screws inserted into the skull may thus enable artificial ears, eyes, noses, and/or wigs to be attached to the appropriate parts of the skull, for example. As an example, a prosthetic attachment (e.g., a nose) may be provided with attractive magnets for attracting the prosthetic attachment to magnetic core bone screws implanted within the bones of the face. The prosthetic attachment may be constructed in such a way so as to provide a protective material layer (e.g., silicone, leather) between the skin and the prosthesis to prevent the raw material of the attractive magnets of the prosthetic attachment from coming in direct contact with the skin. Thus, an advantage is that because no metal or magnetic material comes into direct contact with the user's skin, any potential irritation from contact with the magnetic material may be avoided.

The magnetic core skull screws implanted into the skull may be either of the free-spinning magnetic ball or the fixed magnet within the screw varieties, as an example. However, using the free-spinning magnetic ball variety may be preferable since less precision is required on the part of the surgeon during insertion of the screw into bone because the magnetic ball may freely align itself with the magnetic field of the attracting magnets of the external prosthesis. As an example, the artificial prosthesis may be removed for sleeping, showering, and spending time around the household, otherwise when the user is not in public. At these times, when the user is not wearing the artificial prosthesis, the user's skin may have a more natural appearance since no magnets or metal may be protruding from the skin. Thus, an advantage of utilizing magnetic core skull screws with prosthetic attachments is that no metal may be visible if the prosthetic attachment is removed.

As another example, the magnetic core bone screws described herein above may be used as an alternative magnetic implant for the correction of pectus excavatum or "sunken/funnel chest," as the condition is commonly known. Magnetic core bone screws of either the fixed or free spinning varieties may be used by a surgeon, as an example. However, the free spinning magnetic ball variety may be preferable since the magnetic ball can freely align itself with the attractive force of external attracting magnets, for example. By implanting several strategically placed magnetic ball core bone screws having varied magnetic field strengths, the surgeon may more artfully correct the breastbone structure than the current magnetic implant systems used to treat pectus excavatum, as an example.

As another example, the magnetic core bone screws described herein may be used as an improved alternative magnetic implant for use with magnetic nanoparticles. Currently, one known method of treating spinal cord tumors utilizes magnetic nanoparticles that carry cytotoxic drugs. Magnetic core bone screws of either the fixed or free spinning varieties may be used as a means for efficiently delivering the drug more proximally to the location of the tumor, as an example. For example, the current method of utilizing magnetic nanoparticles involves implanting the magnet in body tissue above the vertebra having the tumor. A magnetic core bone screw may be placed within the vertebra having the tumor, such that the medication in the magnetic core bone screw is concentrated closer to the spinal cord tumor site where the medication is needed.

As described previously throughout this disclosure above, the magnetic core bone screw may comprise a screw cap removably associated with the bone screw, the screw cap being adapted to be screwed into the screw head, as an example. As described as an advantage, the screw cap may completely encase the magnet or magnetic ball contained within the bone screw when the screw cap is screwed into the screw head, such that no magnetic material may contact the bone and/or surrounding tissue, which could cause a bodily rejection of the bone screw and thus infection. Additionally, the screw cap may be adapted to be removable, whilst the bone screw is implanted into bone, such that the magnet or magnetic ball contained within may be removed without necessitating removal of the bone screw from the bone. Such a procedure may allow for the replacement of the existing magnet within the bone screw with a new magnet having a greater strength, which may be advantageous or necessary for certain bone alignment/realignment applications, as described previously herein.

While the screw cap described herein may possess the advantages outlined above, the screw cap may be susceptible to possible leakage or flow of natural bodily fluids gathering around the bone screw after implantation (i.e., during use). The bodily fluids may enter the chamber of the magnetic core bone screw via miniscule openings between the screw head and cap threads, which may inhibit proper functioning of the magnet within the chamber (e.g., the self-alignment of the magnetic ball). Moreover, the bodily fluids may cause the screw cap to come loose and eventually detach from the screw head altogether, exposing the surrounding bone and tissue to the potentially unsafe magnetic material of the magnet. Furthermore, should the magnet within the bone screw be caused to exit the interior cavity, via an opening created by the unattached screw cap, the bone screw will no longer be pulled by an exterior magnetic field (e.g., induced from a correction abacus or neighboring bone screw), and thus the bone (vertebra) will not be caused to shift and correct itself, as desired. As described previously when referring to FIGS. 11A-11B, the bone screw chamber may be provided with a viscous material (e.g., oil or grease) for decreasing rapid and sharp movements of the magnetic ball within the screw chamber. Should the screw cap come undone due to the seepage of bodily fluids in through the tight crevices of the cap threads, the viscous material could also leak out into the body, which could lead to infection and/or other complications. Such complications would ultimately require additional corrective surgery and the replacement of the bone screw already implanted in the bone. Thus, there is a need for an improved screw cap configured to establish a liquid-proof (i.e., waterproof) seal with the screw head, such that to prevent the seepage of bodily fluids, while also being removable from the screw head, as needed.

Figures 20A, 20B:
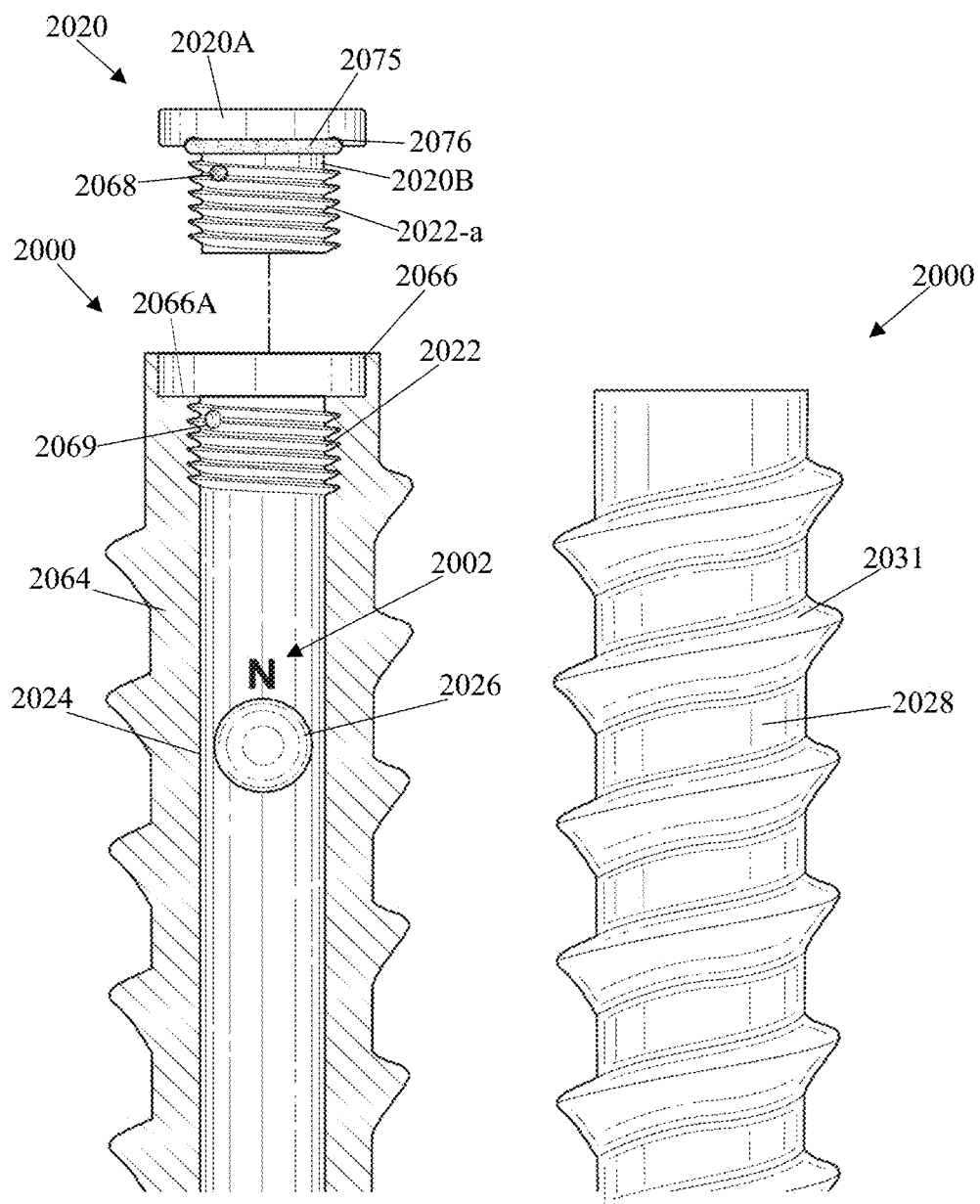
FIGS. 20A-20B illustrate a side sectional view and a side view, respectively, of a portion of the magnetic core bone screw 1100 of FIGS. 11A-11B, having an alternative embodiment for the screw cap and the screw head, respectively, according to an aspect.

FIGS. 20A-20B illustrate a side sectional view and a side view, respectively, of a portion of the magnetic core bone screw 1100 of FIGS. 11A-11B, having an alternative embodiment for the screw cap 2020 and the screw head 2066, respectively, according to an aspect. As described similarly when referring to FIGS. 11A-11B, the bone screw 2000 may include a screw head 2066, which may be associated with a screw cap 2020, a shaft 2064, and a distalmost tip (not shown) disposed at the opposite end of the head 2066, which may be pointed to aid in the drilling and the insertion of the bone screw 2000 into a bone. The shaft 2064 may extend between the head 2066 and the tip (not shown), as an example. The bone screw 2000 may be provided with an inner cavity or chamber 2024 for housing a magnet or magnetic ball 2026, which may thus become the magnetic core of the bone screw 2000, as described previously above. The magnetic ball 2026 may, for example, be neodymium, or any other suitable material. As an example, the magnetic ball 2026 may be housed within the chamber 2024 located in the shaft 2064 of the bone screw 2000, as shown. The magnetic ball 2026 having a north pole 2002 and a south pole (not shown) may be placed in the interior cavity 2024 of the bone screw 2000, as shown in FIG. 20A, such that the magnetic ball 2000 is not visible from the exterior of the screw, as shown by FIG. 20B. The exterior casing 2028 of the screw 2000, which may completely surround and encase the magnet 2026, may be constructed from a material not likely or less likely to be rejected by the human body, such as, for example, titanium or ceramic materials. Thus, an advantage may be that additional coatings may not be needed on the magnet itself, thus reducing the risk of rejection of materials by the patient's body. A complete encasing of the magnet 2026 by the exterior casing 2028 may thus reduce the risk to a patient of injury, rejection of implanted materials, or complications following a surgery.

The bone screw 2000 may also be provided with a set of interior/inner threads 2022 at a top end of the screw within the head 2066, and the inner threads 2022 may be threaded or associated with the cap threads 2022-a lining a body or bottom 2020B of the top screw cap 2020, as shown. The cap 2020 may then seal in the magnetic ball 2026, such that no portion of the magnet 2026 is exposed or visible outside of the exterior casing 2028 of the bone screw 2000, as similarly mentioned above. The screw cap 2020 may be constructed from the same or similar material (e.g., titanium) as the exterior casing 2028, as an example. The cap 2020 may allow for the magnet 2026 to be removably inserted into the bone screw 2000, and replaced or repositioned as needed, for example. As shown by FIG. 20B, the bone screw 2000 may be provided with exterior threads 2031 lining the exterior casing 2028 surface, which may aid a user in screwing, drilling, or otherwise inserting the bone screw 2000 into bone.

As mentioned above, the screw cap 2020 may be configured for establishing a tight seal with the screw head 2066, such that bodily fluids and other liquids may be prevented from entering or exiting the chamber 2024 when the bone screw 2000 is in use within the body. As shown in FIG. 20A, the alternative embodiment of the screw cap 2020 may be provided with an O-ring ("O-ring," "leakage ring") 2075, which may be constructed of medical grade rubber, such as, for example, silicon or ethylene propylene (EPDM). It should be understood that the material used to construct the leakage ring 2075 should be appropriately selected, such that the screw cap 2020 screwed into the screw head 2066 is not harmful when in use (i.e., when the bone screw has been implanted into bone). As an example, the O-ring 2075 may be contained integrally within an annular recess 2076 disposed concentrically in an upper or top portion 2020A of the screw cap 2020, as shown in FIG. 20A. As shown, the annular recess 2076 may line a bottom edge of the screw cap top 2020A such that the O-ring 2075 is caused to at least partially protrude downwardly, such that the friction-like texture from the O-ring 2075 surface may establish a tight, liquid-proof seal with an interior 2066A of the screw head 2066 when the screw cap 2020 is screwed in. As mentioned above, the tight, liquid-proof seal may prevent bodily fluids from entering the screw chamber 2024 and loosening the screw cap 2020 within the screw head 2066, which would potentially expose the magnet 2026 and other material to the bone and surrounding tissue. The exposed magnetic material 2026 (and any viscous material provided in the chamber 2024) may cause a rejection of the implanted bone screw 2000 and could cause infection, necessitating additional surgeries to remove and replace the defective bone screw and treat such infection, as an example. In addition, the tight, liquid-proof seal may prevent seeped fluids from inhibiting motion and movement of the magnet 2026 contained within the chamber 2024, which could affect the bone screw's intended purpose of shifting bones or relieving pressure, as an example.

Thus, an advantage is that the screw cap may establish a tight, liquid-proof seal such that no fluids may enter or exit the screw chamber, preventing any loosening of the screw cap or inhibition of magnetic movement. Another advantage may be that the complete encasing of the magnet within the screw may reduce the potential for rejection by the body, such that implantation of strongly magnetic material into the bone using a minimally invasive technique may be achieved while reducing risk of rejection of the implanted materials in the patient. An additional advantage may then be that the need to perform additional surgeries to remove and replace the implanted bone screw may be negated.

As shown in FIG. 20A, the screw cap 2020 may further comprise a locking pellet ("locking pellet," "locking bead," "pellet," "bead") 2068 integrally associated with at least one of the set of cap threads 2022-a of the screw cap 2020. As an example, the locking bead 2068 may be constructed of a thermoplastic material like nylon, for example, such that the locking bead 2068 may bend and/or squish, but will not break or crack, while the screw cap 2020 is being screwed into the screw head 2066. As an example, the locking bead 2068 may alternatively be provided as a locking patch (not shown) or locking stripe (not shown) lining at least one of the set of cap threads 2022-a. As shown, the screw head 2066 may be provided with a corresponding circular recess ("circular recess," "recess," "circular slot") 2069 integrally disposed within at least one of the inner threads 2022 for receiving the locking bead 2068, as an example. The circular slot 2069 may also be provided with a thermoplastic material like nylon, for example, at least partially wedged into the circular slot 2069. As an example, when the screw cap 2020 is inserted into the screw head 2066 and then caused to twist into the screw head 2066 by an abutting of the cap threads 2022-a along the corresponding inner threads 2022, the locking bead 2068 may enter and lock into the circular recess 2069, such that the screw cap 2020 is fully secured within the screw head 2066. The thermoplastic material (e.g., nylon) of the locking bead 2068 and a portion of the circular recess 2069 engage and compress into one another, such that the locking bead 2068 and the circular recess 2069 exude a positive resistance to loosening. It should be understood that the locking bead 2068 and the recess 2069 may each be disposed integrally in an upper thread portion of the cap threads 2022-a and the inner threads 2022, respectively, as shown, such that the screw cap 2020 is fully inserted into the screw head 2066 before locking in place, as described above. Thus, the screw cap 2020 may only be unscrewed from the screw head 2066 when the locking bead 2068 is physically withdrawn from the recess 2069, which may only occur via a considerable external force, such as the counterclockwise twisting of a Phillips-head screwdriver within the screw cap 2020, for example (see e.g., FIG. 2).

The leakage ring 2075 contained within the annular recess 2076, the locking bead 2068, and the circular recess 2069 disclosed herein above may thus form a bone screw safety system ensuring that the magnet 2026 within the bone screw remains completely encased within the screw chamber 2024, and thus that the screw cap 2020 is kept securely fastened to the screw head 2066. As an example, in the rare event that fluids seep in between the tight threads 2022-a, 2022 (e.g., due to an unexpected failure of the O-ring 2075) and enter the chamber 2024, the locking bead 2068 and the circular recess 2069 may continue to securely maintain the screw cap 2020 within the screw head 2066, such that the screw cap 2020 is prevented from coming loose or undone. The locking bead 2068 and the corresponding circular recess 2069 may thus provide the disclosed bone screw 2000 with a failsafe, such that to ensure the screw cap 2020 remains locked within the screw head 2066 during use, as an advantage. Another advantage may be that the complete encasing of the magnet within the bone screw may reduce the potential for rejection by the body, such that implantation of strongly magnetic material into the bone using a minimally invasive technique may be achieved while reducing risk of rejection of the implanted materials in the patient. An additional advantage is that the disclosed bone screw safety system may be adapted into any of the disclosed magnetic core bone screws having screw caps.

As mentioned above, the magnetic core bone screw 2000 may be thus adapted such that the magnet 2026 within the screw chamber 2024 may be replaced, as needed, after the bone screw 2000 has already been implanted into bone (to provide the bone screw with a stronger magnet, for example). Referring back to FIG. 2, the screw cap 220 and the screw head 266 may each comprise a screw drive or recess for receiving a driving tool or driver, as an example. For example, let the screw cap 220 comprise a Phillips head 230 and let the screw head 266 comprise an Allen head 232, as shown in FIG. 2. In the event that it is desired to remove the screw cap 220 such that to replace the magnet (e.g., 2026) contained within the screw chamber (e.g., 2024), for example, the user (e.g., a surgeon or doctor) may utilize a wrench, for example, or any other suitable driving means, to stably grip onto the Allen head 232 of the screw head 266, as an example. Then, the user may utilize a Phillips-head screwdriver, for example, or any other suitable driving means, to engage the Phillips head 230 of the screw cap 220, and then cause a counterclockwise twisting of the screw cap 220, such that to unscrew the screw cap 220 from the screw head 266. Simultaneously gripping the Allen head 232 of the screw head 266 while unscrewing the screw cap 220, for example, may ensure that the bone screw 200 remains implanted in the bone (i.e., that the bone screw is not also unscrewed or altered). As an example, should the bone screw 200 also be caused to unscrew and/or change its position within the bone, any bone tissue regrowth progressing around and/or on the bone screw surface may be lost or hindered. Thus, the magnet, shown by 2026 in FIG. 20A, may be replaced, as needed, and the screw cap 2020 may be securely reinserted into the screw head 2066 and subsequently screwed back and locked into place, such that the locking bead 2068 reengages with the circular recess 2069, as similarly described above. Thus, an advantage is that the screw cap may safely and securely be removed from the screw head without altering the position of the bone screw already implanted into bone.

It should be understood that the screw cap 2020 shown in FIG. 20A is depicted in a partially sectional view, such that the O-ring 2075 is completely visible. It should be understood that the bone screw 2000 shown in FIGS. 20A-20B may be adapted to comprise only the O-ring 2075 and annular recess 2076, or only the locking bead 2068 and circular recess 2069, pair. However, for the reasons outlined above, it is preferable that the bone screw disclosed herein comprise both the O-ring 2075 and annular recess 2076 and the locking bead 2068 and circular recess 2069 pairs. It should also be understood that the O-ring 2075 and the annular recess 2076 may be provided in an alternative location of the bone screw 2000 than that shown, such as, for example, along an interior of the screw head 2066. Likewise, the locking pellet 2068 and the circular recess 2069 may be configured to be switched, such that the cap threads 2022-a are adapted to have the circular recess 2069 and the interior threads 2022 are adapted to have the locking pellet 2068, as an example. It should also be understood that the locking pellet 2068 may be constructed of other durable, bendy materials other than nylon, such as rubber, for example. It should also be understood that the circular slot 2069 need not be provided with the aforementioned thermoplastic material for the locking of the screw cap 2021 to be achieved.

Figure 21:
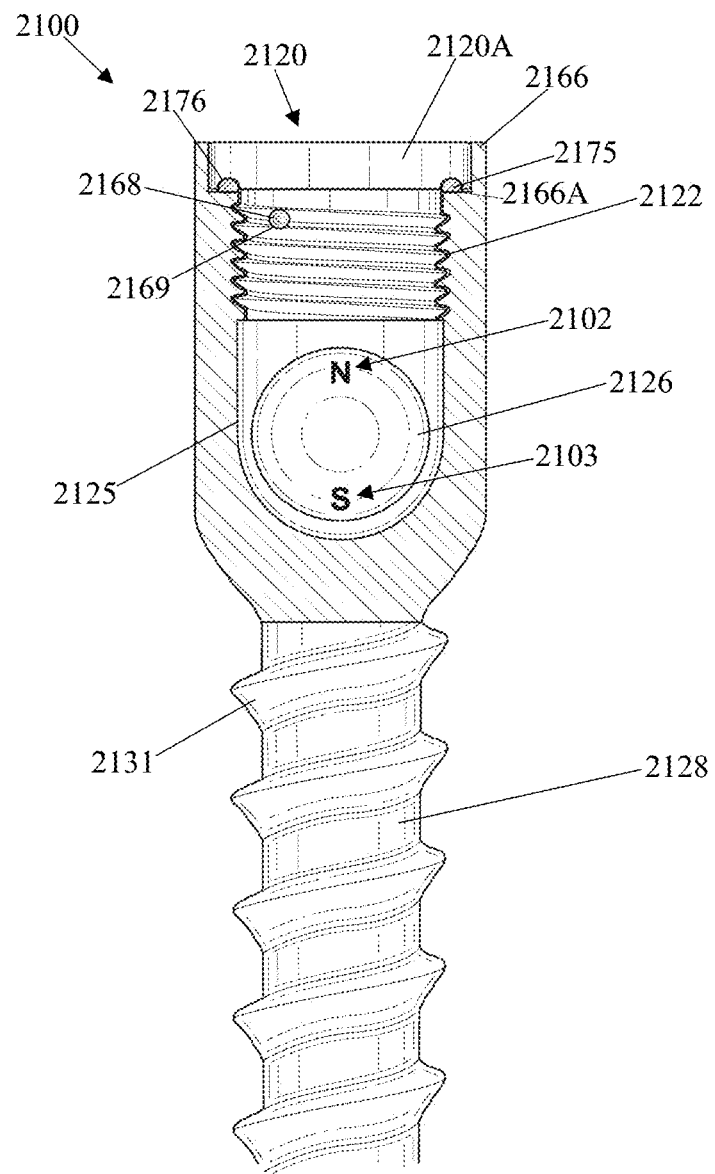
FIG. 21 illustrates a side partially sectional view of a portion of the magnetic core bone screw 1200 of FIG. 12, having an alternative embodiment for the screw cap and the screw head, respectively, according to an aspect.

FIG. 21 illustrates a side partially sectional view of a portion of the magnetic core bone screw 1200 of FIG. 12, having an alternative embodiment for the screw cap 2120 and the screw head 2166, respectively, according to an aspect. As described previously when referring to FIG. 12, the magnetic ball core bone screw 2100 may be provided with a spherical cavity 2125 located within the head 2166 of the bone screw 2100. As shown, the spherical cavity 2125 may be configured to house a magnetic ball 2126 having a north pole 2102 and a south pole 2103. As shown as an example, the magnetic ball 2126 may be placed as a floating magnet within the spherical cavity 2125, allowing the magnet 2126 to freely spin within the cavity 2125. As mentioned previously above, the magnet 2126 may freely spin to align itself with the magnetic field of a neighboring magnet within a neighboring bone screw, or to align itself within an exterior magnetic field (e.g., a magnetic field induced outside of the body). In this view, the screw cap 2120 is shown screwed into the screw head 2166, thus forming a seal via the associated threads 2122 and completely encasing the magnet 2126 within the spherical cavity 2125, as shown as an example. A complete encasing of the magnet 2126 by the screw cap 2120 may reduce the risk to a patient of injury, rejection of implanted materials, or complications following a surgery, as similarly described above. As previously described when referring to FIG. 12, the bone screw 2100 may be provided with a pointed tip (not shown) and exterior threads 2131 wrapping the body 2128 of the bone screw 2100 for facilitating insertion of the bone screw 2100 into bone. The head 2166 of the screw 2100 may be configured to receive a driver (e.g., end of a screwdriver or wrench) for driving the screw 2100 into bone (e.g., vertebrae) and/or for helping facilitate removal of the screw cap 2120 from the screw head 2166, as described previously above when referring to FIGS. 20A-20B. As similarly described above, the bone screw 2100 may be made from a suitable material such as titanium or ceramic and the magnet 2126 may be made of neodymium, as examples, such that to reduce the risk of internal infection or the body rejecting the bone screw altogether.

As similarly described when referring to FIGS. 20A-20B above, a top portion 2120A of the screw cap 2120 may be provided with a recessed integral O-ring 2175 at least partially contained within a concentric annular recess 2176, as shown. As shown, the head 2166 may be configured to comprise a flat interior surface 2166A, such that to firmly contact the O-ring 2175 of the screw cap 2120. It should be understood that either or both the screw cap 2120 and the screw head 2166 may be adapted to comprise an annular recess, as an example. As mentioned above, the O-ring 2175 may protrude downwardly, and may be constructed of a medical grade rubber-like material, such that to form a liquid-proof seal between the screw cap 2120 and the screw head 2166 when the screw cap 2120 is screwed into the screw head 2166, as an example. As shown, the leakage ring 2175 may tightly compress against the flat interior 2166A, such that bodily fluids and other liquids are prevented from entering or exiting the spherical cavity 2125, as an example. As described above, liquids entering the spherical cavity 2125 could inhibit the magnetic ball's 2126 ability to rotate itself such that to align the poles 2102, 2103 within an external magnetic field, which would thus nullify the intended effects of the bone screw(s) implanted in the bone(s). As also described above, the aforementioned liquids could lubricate the joined threads 2122 of the screw cap 2120 and the interior of the screw head 2166, which could allow the screw cap 2120 to come loose and/or detach overtime, exposing the magnetic ball 2126 to the surrounding tissue, which could cause infection, for example. Thus, the leakage ring 2175 may provide the bone screw 2100 with a vital means by which to form a tight seal, such that no liquid or fluid is permitted to enter the spherical cavity 2125.

As shown in FIG. 21, the bone screw 2100 may further be provided with a locking bead 2168 and a corresponding circular recess 2169, as similarly discussed when referring to FIGS. 20A-20B. As shown, when the screw cap 2120 is fully inserted and screwed into the screw head 2166, the locking bead 2168 may be engaged with the circular recess 2169. As mentioned above, the locking bead 2168 may be integrally disposed in an upper thread portion of the set of cap threads, and the circular recess may also be integrally disposed in an upper thread portion of the interior threads of the screw head 2122, such that the locking bead 2168 may lock into the recess 2169 when the cap threads are completely threaded with the interior threads 2122, as shown. As similarly described above when referring to FIGS. 20A-20B, the locking bead 2168 may only be caused to disengage from the circular recess 2169 by the physical exertion of an external force (e.g., the counterclockwise twisting of a driver tool engaged with the top of the screw cap). Thus, the screw cap 2120 may be kept secured to the bone screw 2100 within the screw head 2166 during use, such that liquids or fluids seeping in between the cap and head threads 2122 will be insufficient to cause a loosening of the screw cap 2120 from the screw head 2166, as an example. As also described previously above, the screw cap 2120 may be removed from the screw head 2166, at a later date as needed, after the bone screw 2100 has been implanted in bone, for replacing the magnetic ball 2126 contained within the spherical cavity 2125, as an example. As outlined when referring to FIGS. 20A-20B above, the user may engage and twist the screw drive (e.g., 230 in FIG. 2) of the screw cap 2120 while simultaneously engaging and stabilizing the screw drive (e.g., 232 in FIG. 2) of the screw head 2166, such that to securely remove the screw cap 2120 from the bone screw 2100.

Thus, an advantage of the magnetic core bone screw shown in FIG. 21 is that the magnet may freely spin within the head of the screw, allowing the magnet to align itself within the magnetic field of a neighboring magnet, causing the vertebrae to realign. Another advantage of the secondary embodiment of the bone screw is that the implanting of the bone screw into the body does not require multiple steps, thus reducing the time necessary to perform the procedure. An additional advantage is that the screw cap may safely and securely be removed from the screw head without altering the position of the bone screw already implanted into bone.

It should be understood that while it is possible for the screw cap to be permanently fused to the screw head (via welding, for example), such an approach prevents any necessary or desired removal and/or replacement of the magnetic ball (or magnet) contained within the spherical cavity (or chamber), as described above. It should also be understood that the above disclosed bone screw safety system (the O-ring, the locking bead, and the circular recess) may be provided in any of the magnetic core bone screw embodiments described herein. Each of the bone screw varieties shown throughout FIGS. 1A-21 may comprise at least either the O-ring and annular recess, or the locking bead and corresponding recess, pair. It should therefore also be understood that, as shown in FIGS. 20A-20B, for example, each of the bone screw varieties may also comprise both the O-ring and annular recess, and the locking bead and recess, pairs. As an example, the magnetic core bone screw disclosed herein above may be constructed to comprise a locking nylon disc integrally incorporated into the interior threads of the head, the locking nylon disc concentrically lining at least one of the interior threads.

As described herein and shown throughout the drawings, the exterior casing or body of each bone screw may be provided with a smooth surface. It should be understood that said surface includes the exterior threads extending between the tip and the screw head. However, the surface texture of the magnetic core bone screws disclosed herein above may each be alternatively configured to be rough or rigid. As is known, following the procedural insertion of the bone screw(s) into the bone (e.g., a vertebra), tissue and growth begin to form around the surface of the bone screw(s). As an example, bone screws having a rough surface texture (e.g., grooved or dimpled) may enhance new bone growth and formation on the surface of the bone screw(s). Thus, for applications where more rapid bone growth is desired, such as, for example, in a patient suffering from minor scoliosis of the spine wherein a reduced implantation period is desired, it may be preferable to provide a magnetic core bone screw having a rough surface texture.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

What is claimed is:

1. A bone screw configured to be screwed into a bone, the bone screw comprising:
    an exterior casing;
    a head having a set of interior threads, the head being configured to receive a first driving means for driving the bone screw into the bone;
    wherein at least one of the set of interior threads comprises a circular slot;
    a tip having a distalmost point configured to be driven into the bone;
    a shaft extending between the head and the tip;
    a magnet having a north pole and a south pole;
    an interior cavity disposed within the bone screw and configured to house the magnet; and
    a cap removably associated with the head, the cap comprising:
        a top end configured to receive a second driving means for inserting the cap into, and removing the cap from, the head;
        a bottom having a set of cap threads, at least one of the set of cap threads comprising a locking bead; and
        a leakage ring concentrically lining an upper portion of the bottom;
    wherein the exterior casing encompasses the tip, the shaft, and at least a portion of the head, and wherein a portion of the exterior casing encompassing the shaft comprises a set of exterior threads; and
    wherein an association of the set of cap threads with the set of interior threads causes the locking bead to be engaged with the circular slot, and thus causes the leakage ring to be compressed within an interior of the head, resulting in the cap being sealed to the head.

2. The bone screw of claim 1, further comprising an annular recess integrally disposed in a bottom of the top end, the annular recess containing at least a portion of the leakage ring.

3. The bone screw of claim 1, wherein the top end of the cap comprises a cross recess configured to receive the second driving means.

4. The bone screw of claim 1, wherein the interior cavity is located within the head.

5. The bone screw of claim 1, wherein the interior cavity is located within, and extends a length of, the shaft.

6. The bone screw of claim 1, wherein the magnet is a magnetic ball, the magnetic ball being free spinning and free moving within the interior cavity, such that the magnetic ball can align itself with an exterior magnetic field.

7. The bone screw of claim 1, wherein the exterior casing is constructed from titanium.

8. The bone screw of claim 1, wherein the locking bead is constructed from nylon.

9. The bone screw of claim 1, wherein the leakage ring is constructed from ethylene propylene.

10. The bone screw of claim 1, wherein the magnet is constructed from neodymium.

11. A bone screw configured to be screwed into a bone, the bone screw comprising:
    a head having a set of interior threads, at least one of the set of interior threads having a circular slot;
    a tip having a distalmost point configured to be driven into the bone;
    a body comprising a set of exterior threads, the body extending between the head and the tip;

a magnet having a north pole and a south pole;
an interior cavity located within the bone screw and configured to house the magnet; and
a cap removably associated with the head, the cap comprising:
 a top end configured to receive a driving means for inserting the cap into, and removing the cap from, the head; and
 a set of cap threads lining a bottom of the cap, at least one of the set of cap threads comprising a locking bead;
wherein an association of the set of cap threads with the set of interior threads causes the locking bead to be engaged with the circular slot, and thus causes the cap to be sealed to the head, such that the magnet is fully encased and completely sealed within the bone screw.

12. The bone screw of claim 11, further comprising a concentric annular recess integrally disposed in a bottom portion of the top end of the cap, the concentric annular recess comprising a leakage ring for establishing a liquid-proof seal between the cap and the head.

13. The bone screw of claim 11, wherein the head further comprises a recess configured to receive a second driving means for driving the bone screw into the bone.

14. The bone screw of claim 11, wherein the magnet is a magnetic ball, the magnetic ball being free spinning within the interior cavity, such that the magnetic ball can align itself with an exterior magnetic field.

15. The bone screw of claim 11, wherein the body, the head, and the tip are constructed from titanium.

16. The system of claim 11, wherein the magnet is constructed from neodymium.

17. A screw cap removably associated with a bone screw, the bone screw comprising: a head having a set of interior threads, at least one of the set of interior threads having a circular slot; a magnet; and an interior cavity located within the bone screw and configured to house the magnet; the screw cap comprising:
 a top end configured to receive a first driving means for inserting the screw cap into, and removing the screw cap from, the head;
 a bottom having a set of cap threads, one of the set of cap threads comprising a locking bead; and
 an annular recess concentrically lining an upper portion of the bottom, the annular recess comprising an integral leakage ring for establishing a liquid-proof seal between the screw cap and the head.

18. The screw cap of claim 17, wherein an association of the set of cap threads with the set of interior threads causes the locking bead to be engaged with the circular slot, and thus causes the leakage ring to be compressed within an interior of the head, resulting in the screw cap being securely sealed to the head.

19. The screw cap of claim 18, further comprising a cross recess disposed on the top end, the cross recess being adapted for receiving the first driving means.

20. The screw cap of claim 19, wherein the head further comprises:
 a hex-shaped recess lining an outer periphery of a top of the head, the hex-shaped recess being adapted to receive a second driving means;
 wherein, after the bone screw has been screwed into a bone, a stable engagement of the hex-shaped recess by the second driving means causes the bone screw to be held in place within the bone, such that a simultaneous rotational engagement of the cross recess by the first driving means causes the screw cap to be removed from the head, such that the magnet within the interior cavity can be replaced, without changing a position of the bone screw within the bone.

21. The screw cap of claim 20, wherein the first driving means is a screwdriver and the second driving means is a wrench.

22. The screw cap of claim 17, wherein the set of interior threads and the set of cap threads each further comprises one of: a nylon bead, a nylon stripe, a nylon patch, and a nylon disc.

23. The screw cap of claim 17, wherein the leakage ring is constructed from silicon.

* * * * *